US009790488B2

(12) United States Patent
Yang

(10) Patent No.: US 9,790,488 B2
(45) Date of Patent: Oct. 17, 2017

(54) MUTATED INTERNAL RIBOSOMAL ENTRY SITE (IRES) FOR CONTROLLED GENE EXPRESSION

(71) Applicant: Agency for Science, Technology and Research, Singapore (SG)

(72) Inventor: Yuansheng Yang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/909,264

(22) PCT Filed: Aug. 1, 2014

(86) PCT No.: PCT/SG2014/000369
§ 371 (c)(1),
(2) Date: Feb. 1, 2016

(87) PCT Pub. No.: WO2015/016786
PCT Pub. Date: Feb. 5, 2015

(65) Prior Publication Data
US 2016/0244746 A1 Aug. 25, 2016

(30) Foreign Application Priority Data

Aug. 2, 2013 (SG) .................................. 201305917

(51) Int. Cl.
| | |
|---|---|
| C12N 15/67 | (2006.01) |
| C12N 15/85 | (2006.01) |
| C12N 15/10 | (2006.01) |
| C12N 15/63 | (2006.01) |
| C12Q 1/68 | (2006.01) |
| C07H 21/04 | (2006.01) |

(52) U.S. Cl.
CPC ......... *C12N 15/1051* (2013.01); *C12N 15/67* (2013.01); *C12N 15/85* (2013.01); *C12N 15/63* (2013.01); *C12N 2840/203* (2013.01)

(58) Field of Classification Search
None
See application file for complete search history.

(56) References Cited

U.S. PATENT DOCUMENTS

| | | | |
|---|---|---|---|
| 2009/0162900 A1 | 6/2009 | Enenkel et al. | |
| 2009/0221681 A1* | 9/2009 | Hochberg .......... | A61K 48/0058 514/44 R |
| 2012/0301919 A1 | 11/2012 | Yang et al. | |
| 2013/0203078 A1* | 8/2013 | Paz-Rojas .......... | G01N 33/5044 435/7.21 |

FOREIGN PATENT DOCUMENTS

| | | |
|---|---|---|
| EP | 2749573 A1 | 7/2014 |
| WO | 2007034487 A1 | 3/2007 |
| WO | 2012018607 A2 | 2/2012 |
| WO | 2013004076 A1 | 1/2013 |

OTHER PUBLICATIONS

Sautter et al., "Selection of High-Producing CHO Cells Using NPT Selection Marker with Reduced Enzyme Activity," Biotechnology and Bioengineering, vol. 89, Oct. 14, 2014, pp. 530-538.
Kriz et al., "A Plasmid-Based Multigene Expression System for Mammalian Cells," Nat. Commun., vol. 1, No. 120, 2010, pp. 1-6.
Ulrich et al., "Exponential Megapriming PCR (EMP) Cloning-Seamless DNA Insertion into Any Target Plasmid without Sequence Constraints," PloS One, vol. 7, No. 12, e53360, Dec. 2012, pp. 1-9.
Kaufman et al., "Improved Vectors for Stable Expression of Foreign Genes in Mammalian-Cells by Use of the Untranslated Leader Sequence From EMC Virus," Nucleic Acids Research, vol. 19, No. 16, 1991, pp. 4485-4490.
Van Berkel et al., "N-linked Glycosylation is an Important Parameter for Optimal Selection of Cell Lines Producing Biopharmaceutical Human IgG," Biotechnology Progress, vol. 25, No. 1, 2009, pp. 244-251.
Koh et al., "An Internal Ribosome Entry Site (IRES) Mutant Library for Tuning Expression Level of Multiple Genes in Mammalian Cells," PloS One, vol. 8, No. 12, e82100, Dec. 2013, pp. 1-9.
Trowitzsch et al., "Light It Up: Highly Efficient Multigene Delivery in Mammalian Cells," Bioessays, vol. 33, 2011, pp. 946-955.
Bieniossek et al, "MultiBac: Expanding the Research Toolbox for Multiprotein Complexes," Trends in Biochemical Sciences, vol. 37, No. 2, Feb. 2012, pp. 49-57.
Fussenegger et al., "Genetic Optimization of Recombinant Glycoprotein Production by Mammalian Cells," Trends in Biotechnology, vol. 17, Jan. 1999, pp. 35-42.
Fussenegger et al., "Regulated Multicistronic Expression Technology for Mammalian Metabolic Engineering," Cytotechnology, vol. 28, 1998, pp. 111-125.
Jensen et al., "Artificial Promoters for Metabolic Optimization," Biotechnology and Bioengineering, vol. 58, Nos. 2 & 3, Apr. 20/May 5, 1998, pp. 191-195.
Leitzgen et al., "Assembly of Immunoglobulin Light Chains as a Prerequisite for Secretion—A Model for Oligomerization-Dependent Subunit Folding," Journal of Biological Chemistry, vol. 272, No. 5, Jan. 31, 1997, pp. 3117-3123.
Lenny et al., "Regulation of Endoplasmic-Reticulum Stress Proteins in COS Cells Transfected With Immunoglobulin-Mu Heavy-Chain cDNA," Journal of Biological Chemistry, vol. 266, No. 30, Oct. 25, 1991, pp. 20532-20537.
Schlatter et al., "On the Optimal Ratio of Heavy to Light Chain Genes for Efficient Recombinant Antibody Production by CHO Cells," Biotechnology Progress, vol. 21, 2005, pp. 122-133.
Tornoe et al., "Generation of a Synthetic Mammalian Promoter Library by Modification of Sequences Spacing Transcription Factor Binding Sites," Gene, Vol. 297, 2002, pp. 21-32.

(Continued)

*Primary Examiner* — Nancy J Leith
(74) *Attorney, Agent, or Firm* — Winstead, P.C.

(57) ABSTRACT

The present invention relates to a nucleic acid molecule comprising one or multiple mutant IRES elements. Further, the present invention relates to methods of enhancing gene expression and to methods of differentially controlling expression of one or multiple gene(s) of interest. In addition, the present invention relates to a kit for studying interactions or any application requiring co-expression of multiple genes.

19 Claims, 11 Drawing Sheets

(56) References Cited

OTHER PUBLICATIONS

Yahata et al., "Multi-Gene Gateway Clone Design for Expression of Multiple Heterologous Genes in Living Cells: Conditional Gene Expression at Near Physiological Levels," J. Biotechnol., vol. 118, 2005, pp. 123-134.

Yang et al., "Mutated Polyadenylation Signals for Controlling Expression Levels of Multiple Genes in Mammalian Cells," Biotechnology and Bioengineering, vol. 102, No. 4, Mar. 1, 2009, pp. 1152-1160.

Fallout et al, "Alternative-Splicing-Based Bicistronic Vectors for Ratio-Controlled Protein Expression and Application to Recombinant Antibody Production," Nucleic Acids Research, vol. 37, No. 20, 2009, pp. 1-10.

Chusainow et al., "A Study of Monoclonal Antibody-Producing CHO Cell Lines: What Makes a Stable High Producer?," Biotechnology and Bioengineering, vol. 102, No. 4, Mar. 1, 2009, pp. 1182-1196.

Ho et al., "IRES-Mediated Tricistronic Vectors for Enhancing Generation of High Monoclonal Antibody Expressing CHO Cell Lines," Journal of Biotechnology, vol. 157, 2012, pp. 130-139.

Lee et al., "A Clone Screening Method Using mRNA Levels to Determine Specific Productivity and Product Quality for Monoclonal Antibodies," Biotechnology and Bioengineering, vol. 102, No. 4, Mar. 1, 2009, pp. 1107-1118.

Eszterhas et al., "Transcriptional Interference by Independently Regulated Genes Occurs in any Relative Arrangement of the Genes and is Influenced by Chromosomal Integration Position," Molecular and Cellular Biology, vol. 22, No. 2, 2002, pp. 469-479.

De Felipe et al, "E unum pluribus: Multiple Proteins from a Self-Processing Polyprotein," Trends in Biotechnology, vol. 24, No. 2, Feb. 2006, pp. 68-75. and supplementary data.

Ho et al., "Comparison of Internal Ribosome Entry Site (IRES) and Furin-2A (F2A) for Monoclonal Antibody Expression Level and Quality in CHO Cells," PLoS One, vol. 8, No. 5, e63247, May 2013, pp. 1-12.

De Felipe et al., "Inhibition of 2A-Mediated 'Cleavage' of Certain Artificial Polyproteins Bearing N-terminal Signal Sequences," Biotechnology Journal, vol. 5, 2010, pp. 213-223.

Kim et al., "High Cleavage Efficiency of a 2A Peptide Derived from Porcine Teschovirus-1 in Human Cell Lines, Zebrafish and Mice," PLoS One, vol. 6, No. 4, e18556, Apr. 2011, pp. 1-8.

Chan et al., "Comparison of IRES and F2A-Based Locus-Specific Multicistronic Expression in Stable Mouse Lines," PLoS One, vol. 6, No. 12, e28885, Dec. 2011, pp. 1-11.

Martinez-Salas, E, "Internal Ribosome Entry Site Biology and Its Use in Expression Vectors," Current Opinion in Biotechnology, vol. 10, 1999, pp. 458-464.

Mountford et al., "Internal Ribosome Entry Sites and Dicistronic RNAs in Mammalian Transgenesis," Trends in Genetics, vol. 11, No. 5, 1995, pp. 179-184.

Hellen et al., "Internal Ribosome Entry Sites in Eukaryotic mRNA Molecules," Genes Dev., vol. 15, 2001, pp. 1593-1612.

Sasaki et al., "Multi-Gene Gateway Clone Design for Expression of Multiple Heterologous Genes in Living Cells: Eukaryotic Clones Containing Two and Three ORF Multi-Gene Cassettes Expressed from a Single Promoter," Journal of Biotechnology, vol. 136, 2008, pp. 103-112.

Liu et al, "Generation of Mammalian Cells Stably Expressing Multiple Genes at Predetermined Levels," Analytical Biochemistry, vol. 280, 2000, pp. 20-28.

Livak et al., "Analysis of Relative Gene Expression Data Using Real-Time Quantitative PCR and the 2-ΔΔCT Method," Methods, vol. 25, 2001, pp. 402-408.

Bochkov et al., "Translational Efficiency of EMCV IRES in Bicistronic Vectors is Dependent upon IRES Sequence and Gene Location," Biotechniques, vol. 41, Sep. 2006, pp. 283-284, 286, 288 passim.

Borman et al., "Picornavirus Internal Ribosome Entry Segments: Comparison of Translation Efficiency and the Requirements for Optimal Internal Initiation of Translation in Vitro," Nucleic Acids Research, vol. 23, No. 18, 1995, pp. 3656-3663.

Borman et al., "Comparison of Picornaviral IRES-Driven Internal Initiation of Translation in Cultured Cells of Different Origins," Nucleic Acids Research, vol. 25, No. 5, 1997, pp. 925-932.

Duke et al., "Sequence and Structural Elements that Contribute to Efficient Encephalomyocarditis Virus-RNA Translation," Journal of Virology, vol. 66, No. 3, Mar. 1992, pp. 1602-1609.

Davies et al., "The Sequence Context of the Initiation Codon in the Encephalomyocarditis Virus Leader Modulates Efficiency of Internal Translation Initiation," J. Virol., vol. 66, No. 4, Apr. 1992, pp. 1924-1932.

Kaminski et al., "Translation of Encephalomyocarditis Virus-RNA—Parameters Influencing the Selection of the Internal Initiation Site," EMBO Journal, vol. 13, No. 7, 1994, pp. 1673-1681.

Mehdi et al., "Initiation of Translation at CUG, GUG, and ACG Codons in Mammalian-Cells," Gene, vol. 91, 1990, pp. 173-178.

Marilyn Kozak, "Context Effects and Inefficient Initiation at Non-AUG Codons in Eucaryotic Cell-Free Translation Systems," Molecular and Cellular Biology, vol. 9, No. 11, Nov. 1989, pp. 5073-5080.

Peabody, D.S., Translation Initiation at Non-AUG Triplets in Mammalian Cells, Journal of Biological Chemistry, vol. 264, No. 9, Mar. 25, 1989, pp. 5031-5035.

Cairns et al., "Utilization of Non-AUG Initiation Codons in a Flow Cytometric Method for Efficient Selection of Recombinant Cell Lines," Biotechnology and Bioengineering, vol. 108, No. 11, Nov. 2011, pp. 2611-2622.

Van Blokland et al., "A Novel, High Stringency Selection System Allows Screening of Few Clones for High Protein Expression," Journal of Biotechnology, vol. 128, 2007, pp. 237-245.

Ng et al., "Application of Destabilizing Sequences on Selection Marker for Improved Recombinant Protein Productivity in CHO-DG44," Metabolic Engineering, vol. 9, 2007, pp. 304-316.

Jiang et al., "Regulation of Recombinant Monoclonal Antibody Production in Chinese Hamster Ovary Cells: A Comparative Study of Gene Copy Number, mRNA Level, and Protein Expression," Biotechnology Progress, vol. 22, 2006, pp. 313-318.

Davies et al., "Impact of Gene Vector Design on the Control of Recombinant Monoclonal Antibody Production by Chinese Hamster Ovary Cells," Biotechnology Progress, vol. 27, No. 6, 2011, pp. 1689-1699.

Gonzalez et al., "Kinetic Model of BiP- and PDI-Mediated Protein Folding and Assembly," Journal of Theoretical Biology, vol. 214, 2002, pp. 529-537.

Aggarwal, S., "What's Fueling the Biotech Engine-2009-2010," Nature Biotechnology, vol. 28, No. 11, Nov. 2010, pp. 1165-1171.

Ho et al., "Control of IgG LC:HC Ratio in Stably Transfected CHO Cells and Study of the Impact on Expression, Aggregation, Glycosylation and Conformation Stability," Journal of Biotechnology, vol. 165, 2013, pp. 157-166.

Li et al.,"Analysis of IgG Heavy Chain to Light Chain Ratio with Mutant Encephalomyocarditis Virus Internal Ribosome Entry Site," Protein Engineering Design & Selection, vol. 20, No. 10, 2007, pp. 491-496.

De Quinto et al., Parameters in Influencing Translational Efficiency in Aphthovirus IRES-based Bicistronic Expression Vectors, Gene, vol. 217, 1998, pp. 51-56.

Bouabe et al., "Improvement of Reporter Activity by IRES-Mediated Polycistronic Reporter System," Nucleic Acids Research, vol. 36, No. 5, e28, 2008, pp. 1-9.

Hennecke et al., "Composition and Arrangement of Genes Define the Strength of IRES-Driven Translation in Bicistronic mRNAs," Nucleic Acids Research, vol. 29, No. 16, 2001, pp. 3327-3334.

Kaminski et al., "Initiation of Encephalomyocarditis Virus-RNA Translation—The Authentic Initiation Site is Not Selected by a Scanning Mechanism," EBMO Journal, vol. 9, No. 11, 1990, pp. 3753-3759.

Kaminski et al., "The Polypyrimidine Tract Binding Protein (PTB) Requirement for Internal Initiation of Translation of Cardiovirus RNAs is Conditional Rather Than Absolute," RNA—A Publication of the RNA Society, vol. 4, Apr. 6, 1998, pp. 626-638.

(56) References Cited

OTHER PUBLICATIONS

International Preliminary Report on Patentability for International Application No. PCT/SG2014/000369 dated Feb. 2, 2016, pp. 1-7.
Written Opinion of the International Searching Authority for International Application No. PCT/SG2014/000369 dated Oct. 9, 2014, pp. 1-5.

* cited by examiner

Figure 1

| SEQ ID NO. | | EMCV IRES 3'-end Sequence 10th 11th 12th | Strength (%) | | | Variant ID |
|---|---|---|---|---|---|---|
| 1 | WT | ATGATAATATGGCCACAACCATG | 100.00 | ± | 0.00 | WT |
| 2 | Mutation to GTG | GTGATAATATGGCCACAACCATG | 90.48 | ± | 0.12 | V1 |
| 3 | | ATGATAATATGGCCACAACCGTG | 83.59 | ± | 1.72 | V3 |
| 4 | | ATGATAATGTGGCCACAACCATG | 35.48 | ± | 3.50 | V7 |
| 5 | | GTGATAATATGGCCACAACCGTG | 67.42 | ± | 2.91 | V4 |
| 6 | | GTGATAATGTGGCCACAACCATG | 29.45 | ± | 1.86 | V10 |
| 7 | | ATGATAATGTGGCCACAACCGTG | 0.98 | ± | 0.02 | V19 |
| 8 | | GTGATAATGTGGCCACAACCGTG | 1.37 | ± | 0.02 | V18 |
| 9 | Mutation to CTG ACG ATA TTG | ATGATAATCTGGCCACAACCATG | 45.18 | ± | 2.12 | V5 |
| 10 | | ATGATAATATAGCCACAACCATG | 39.91 | ± | 0.80 | V6 |
| 11 | | ATGATAATTTGGCCACAACCATG | 34.39 | ± | 0.72 | V8 |
| 12 | | ATGATAATACGGCCACAACCATG | 33.25 | ± | 0.36 | V9 |
| 13 | | ATGATAATCTGGCCACAACCCTG | 9.47 | ± | 1.90 | V13 |
| 14 | | CTGATAATCTGGCCACAACCCTG | 13.58 | ± | 1.50 | V12 |
| 15 | | ATGATAATACGGCCACAACCACG | 4.02 | ± | 0.87 | V14 |
| 16 | | ACGATAATACGGCCACAACCACG | 3.23 | ± | 0.18 | V15 |
| 17 | | ATGATAATATAGCCACAACCATA | 1.79 | ± | 0.09 | V16 |
| 18 | | ATAATAATATAGCCACAACCATA | 1.67 | ± | 0.16 | V17 |
| 19 | | ATGATAATTTGGCCACAACCTTG | 0.58 | ± | 0.09 | V22 |
| 20 | | TTGATAATTTGGCCACAACCTTG | 0.81 | ± | 0.03 | V20 |
| 21 | | ATTATAATATTGCCACAACCATT | 0.69 | ± | 0.02 | V21 |
| 22 | Deletion | ATGATAATATG | 86.42 | ± | 0.03 | V2 |
| 23 | | ATG | 24.35 | ± | 4.04 | V11 |
| 24 | Deletion and mutation | ATGATAATGTG | 0.34 | ± | 0.20 | V25 |
| 25 | | GTGATAATGTG | 0.46 | ± | 0.10 | V24 |
| 26 | | GTG | 0.57 | ± | 0.12 | V23 |

Figure 2

| Start condon | Cap-dependent | EMCV IRES 11th | EMCV IRES 11th,12th | EMCV IRES 10th, 11th, 12th |
|---|---|---|---|---|
| AUG | 100 | 100.00 ± 0.00 | 100.00 ± 0.00 | 100.00 ± 0.00 |
| CUG | 50 | 45.18 ± 2.12 | 9.47 ± 1.90 | 13.58 ± 1.50 |
| GUG | 20 | 35.48 ± 3.50 | 0.98 ± 0.02 | 1.37 ± 0.02 |
| ACG | 10 | 33.25 ± 0.36 | 4.02 ± 0.87 | 3.23 ± 0.18 |
| AUA | 5 | 39.91 ± 0.80 | 1.79 ± 0.09 | 1.67 ± 0.16 |
| UUG | ND | 34.39 ± 0.72 | 0.58 ± 0.09 | 0.81 ± 0.03 |

Cap-dependent translation efficiencies of non-AUG condons were determined in COS-1 cells in transient transfections.

Figure 3
(A)
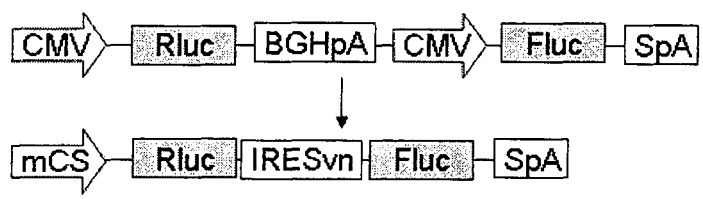
(B)
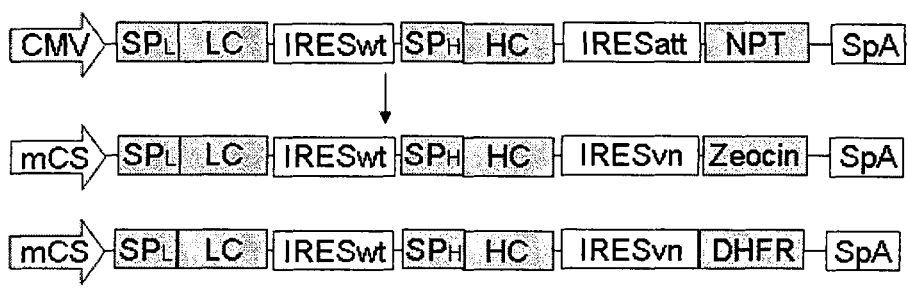
(C)
                                                    DHFR
HP: GCTCGACAGCC<u>ATG</u>GCTGGCTTGGC<u>ATG</u>
(D)
SP$_L$: MDMRVPAQLLGLLLLWLSGARC
LC: DIQMTQSPSSLSASVGDRVT...EVTHQGLSSPVTKSFNRGEC
SP$_H$: MELGLSWIFLLAILKGVQC
HC: EVQLVESGGGLVQPGGSLRL... MHEALHNHYTQKSLSLSPGK Figure 6
(A)
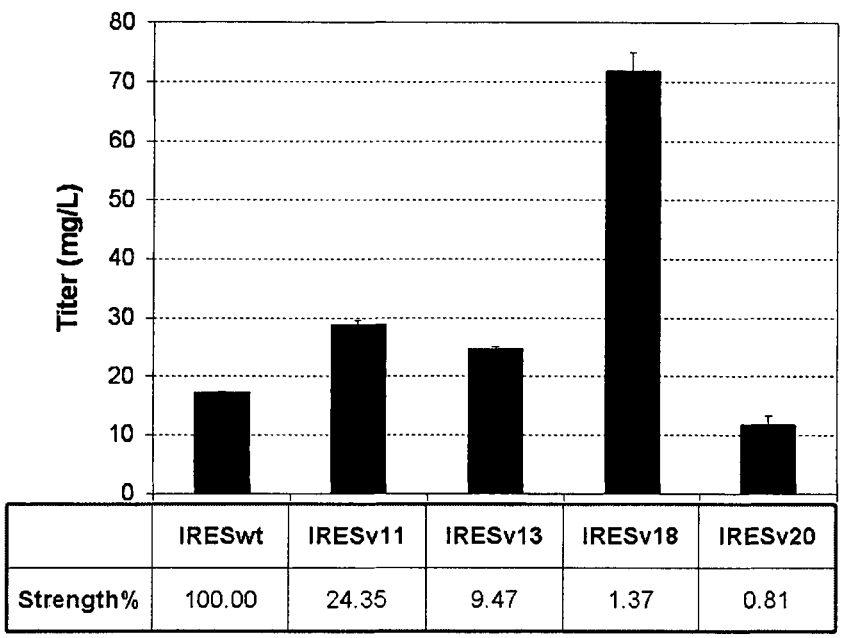
(B)
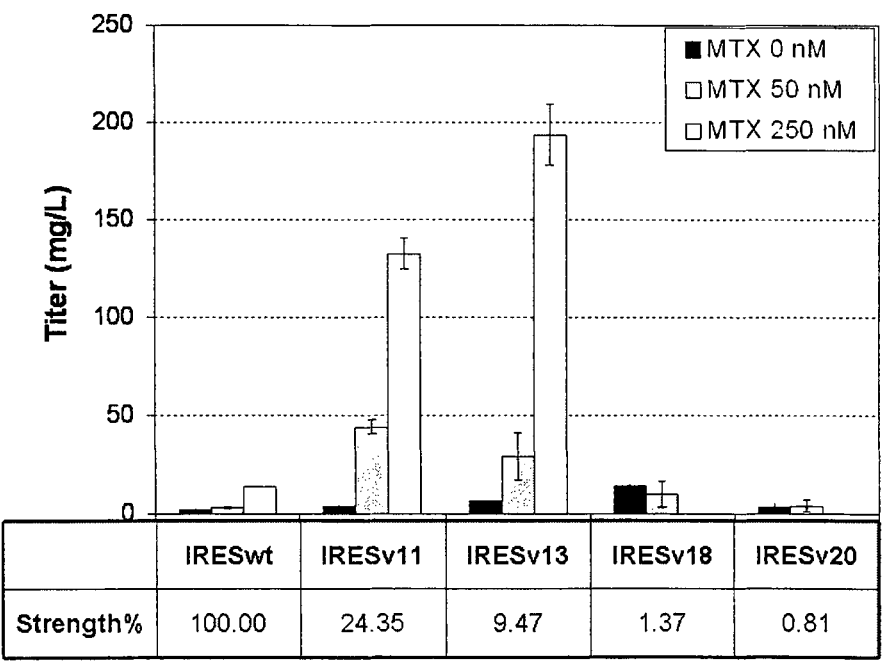

Figure 10
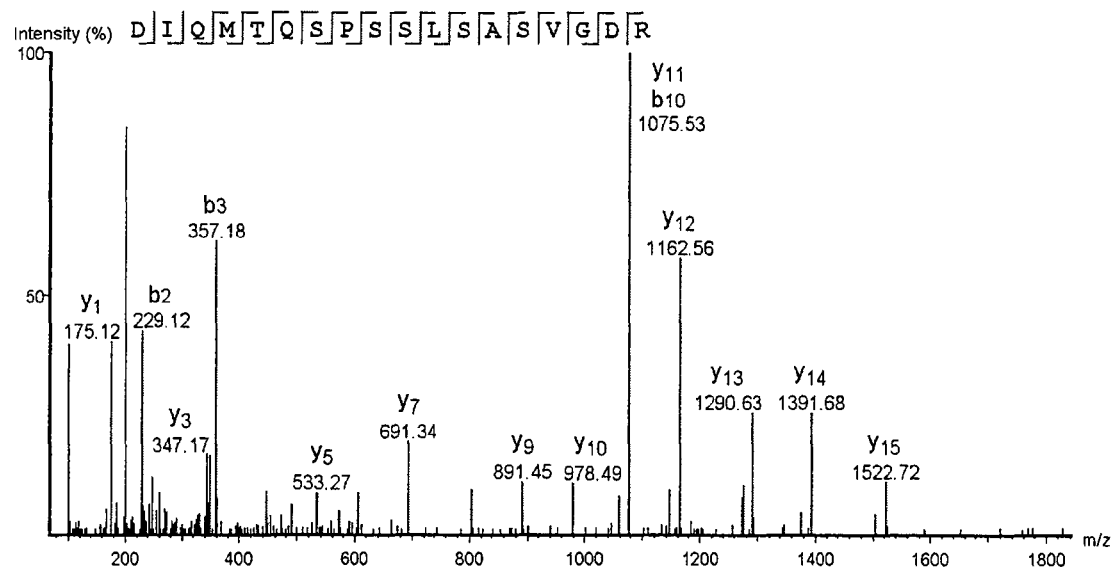
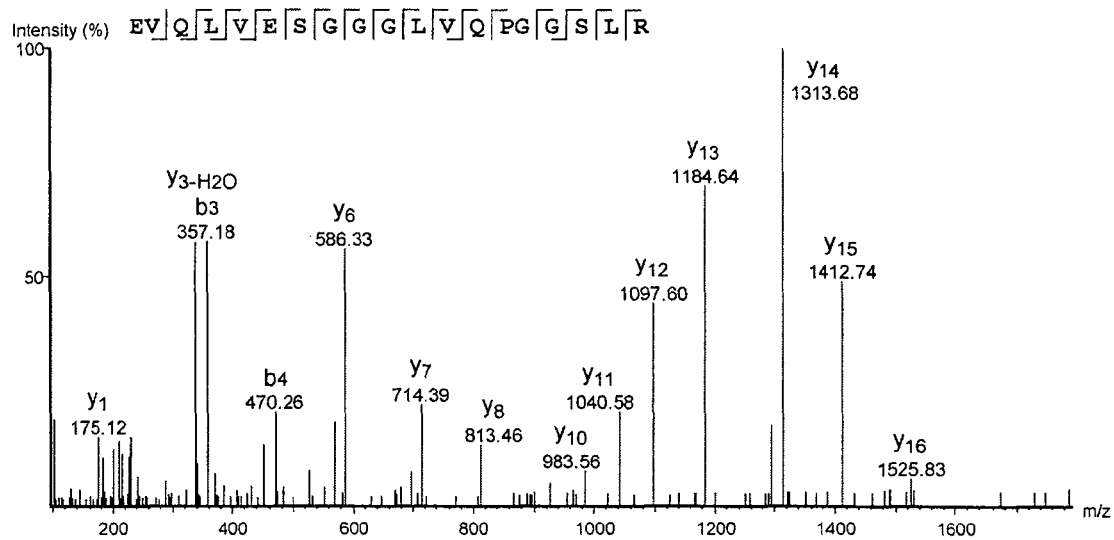

MUTATED INTERNAL RIBOSOMAL ENTRY SITE (IRES) FOR CONTROLLED GENE EXPRESSION

FIELD OF THE INVENTION

The present invention lies in the field of molecular biology and relates to a nucleic acid molecule comprising one or more mutant IRES elements. Further, the present invention relates to methods of identifying cells that provide for enhanced gene expression and to methods of differentially controlling expression of two or more genes of interest. In addition, the present invention relates to a kit for differential expression of multiple genes.

BACKGROUND OF THE INVENTION

Simultaneous expression of multiple genes in mammalian cells at finely controlled amounts or ratios is required for applications such as synthetic biology, investigating interactions between proteins and its complexes, cell engineering, multi-subunit protein production, gene therapy, and reprogramming of somatic cells into stem cells [Trowitzsch, S. et al. (2011) Bioessays, 33, 946-955; Bieniossek, C. et al. (2012) Trends in Biochemical Sciences, 37, 49-57]. Three common strategies for controlling multiple gene expression in mammalian cells are (i) co-transfection of multiple vectors at different relative amounts [Schlatter, S. et al. (2005) Biotechnology Progress, 21, 122-133], (ii) single vector having promoters with different strength [Yahata, K. et al. (2005) J. Biotechnol., 118, 123-134] or applying different polyadenylation signals to each gene [Yang, Y. S. et al. (2009) Biotechnology And Bioengineering, 102, 1152-1160], and (iii) insertion of splicing signals with varied splicing efficiencies between genes [Fallot, S. et al. (2009) Nucleic Acids Research, 37]. Co-transfection is an inaccurate approach as the relative amount of different genes incorporated into cells varies from cell-to-cell due to variations in transfection efficiency [Chusainow, J. et al. (2009) Biotechnol Bioeng, 102, 1182-1196; Ho, S. C. L. et al. (2012) Journal of Biotechnology, 157, 130-139]. Using a single vector with multiple promoters ensures introduction of different genes into each cell at identical amounts and provides accurate control of gene expression in transient transfections [Yahata, K. et al. (2005) J. Biotechnol., 118, 123-134]. However, the expression ratio between the products of the different genes still varies between cells in a stably transfected cell pool [Lee, C. J. et al. (2009) Biotechnology And Bioengineering, 102, 1107-1118] as the arrangement of multiple promoters in close proximity causes transcriptional interference, where the active expression of one gene suppresses expression of the other genes. Moreover, the degree of suppression of each gene depends on the integration site in the genome [Eszterhas, S. K. et al. (2002) Molecular and Cellular Biology, 22, 469-479]. The use of splicing signals allows stricter control of relative gene expression in both transient and stable transfections as all genes are expressed in one transcript [Fallot, S. et al. (2009) Nucleic Acids Research, 37]. Nonetheless, this method is difficult to use because cryptic splicing sites in protein coding sequences need to be eliminated.

Co-expression of multiple genes from one mRNA for strict control of the relative gene expression can also be achieved by using either 2A elements or internal ribosome entry site (IRES). 2A linked genes are expressed in one single open reading frame (ORF) and "self-cleavage" occurs co-translationally to give equal amounts of co-expressed proteins [de Felipe, P. et al. (2006) Trends in Biotechnology, 24, 68-75]. This method does not allow modulation of the expression ratio between the proteins of interest. Moreover, incomplete cleavage of 2A peptides often results in the attachment of unwanted residues to the proteins of interest and formation of fusion proteins [Ho, S. C. L. et al. (2013) Plos One, 8, e63247].

When IRES elements are included between multiple ORFs, the first ORF is translated by the canonical cap-dependent mechanism while the rest are translated through a cap-independent mechanism [Chan, H. Y. et al. (2011) PLoS One, 6]. Encephalomyocarditis virus (EMCV) IRES is the most widely used IRES for multiple gene expression in mammalian cells because of its superior activity in different cell lines and ability to mediate accurate translation [Bochkov, Y. A. and Palmenberg, A. C. (2006) Biotechniques, 41, 283-284, 286, 288 passim.]. The region that contributes to efficient EMCV IRES translation contains twelve AUGs triplets [Duke, G. M. et al. (1992) Journal of Virology, 66, 1602-1609]. Translation initiation occurs primarily at the 11th AUG (AUG-11), partially at the 12th AUG (AUG-12), and almost none at the 10th AUG (AUG-10) [Kaminski, A. et al. (1994) Embo Journal, 13, 1673-1681].

It has been shown that IRES allows strict control of the relative gene expression in both transient and stable transfections [Ho, S. C. L. et al. (2012) Journal of Biotechnology, 157, 130-139]. In contrast to the 2A element, products generated using IRES does not form any undesirable fusion proteins [Ho, S. C. L. et al. (2013) Plos One, 8, e63247]. More importantly, as genes are translated independently, the relative expression of different genes can be adjusted by varying the strength of IRES applied on each gene. Using naturally available IRES could be a choice, but the modulation range of the expression levels for the different genes is narrow due to the lack of sufficient IRES elements [Sasaki, Y. et al. (2008) Journal of Biotechnology, 136, 103-112]. Generation of a synthetic IRES library based on random mutagenesis can widen the range of IRES activity. In the prior art a set of eleven IRES mutants was generated by error prone PCR which allows controlled gene expression level across a 20-fold range [Livak, K. J. and Schmittgen, T. D. (2001) Methods, 25, 402-408]. However, the strengths of these IRES mutants appear to be cell specific as the relative expression of four IRES mutants significantly varied between expression in HEK293T cells and CHO K1 cells.

Thus, no multiple gene expression controlling system that is based on IRES elements is known in the art wherein the different genes can be controlled individually over a wide range of relative expression and which demonstrates stable expression in different cell lines. Nonetheless, there is need in the art for such system in synthetic biology and cell engineering, multi-subunit protein production, gene therapy, and reprogramming of somatic cells into stem cells.

SUMMARY OF THE INVENTION

It is an object of the present invention to meet the above need by providing an expression system as described herein. Surprisingly, the inventors have found that the IRES translation initiation codons, in particular the 10th, 11th, and 12th AUG of the Encephalomyocarditis virus (EMCV) IRES, can be deleted or mutated to non-AUG triplets with the thus mutated IRES mediating decreased protein expression. It was further found that mutated AUG triplets that gradually decrease cap-dependent translation (CUG, GUG, ACG, AUA, AUU, UUG) are also effective in IRES dependent translation. Thus, by varying the type and number of mutations of IRES translation initiation codons the translation of multicistronic mRNA can be systematically and gradually controlled, in particular decreased. As each gene of the multicistronic mRNA is linked to its own IRES, each gene can be controlled individually.

In a first aspect, the invention thus relates to a nucleic acid molecule comprising a first IRES sequence, wherein the IRES sequence is a mutant IRES sequence and comprises or consists of a nucleotide sequence selected from the group consisting of any one of the nucleotides sequences set forth in SEQ ID Nos. 2-26. The mutated IRES sequence allows reduced expression of a gene of interest and may thus be used for differential control of gene expression. For example, if the first attenuated IRES sequence controls translation of a first gene of interest, such as a selection marker, the expression of this selection marker may be differentially decreased compared to other genes of interest on the same multicistronic element which are, for example, controlled by wildtype IRES sequences or, more generally, by non-attenuated control elements.

In another aspect, the invention relates to host cells that comprise the nucleic acid molecules of the invention.

In a further aspect, the invention is directed to methods of identifying cells, preferably recombinant cells, that provide for enhanced gene expression comprising the steps of:

(i) constructing a cell-based expression system comprising a promoter, a gene encoding for a selection marker, one or more genes of interest different from the selection marker gene, and a mutant IRES sequence that comprises or consists of a nucleotide sequence selected from the group consisting of any one of the nucleotides sequences set forth in SEQ ID Nos. 2-26, wherein the mutant IRES sequence is operably linked to the gene encoding for a selection marker but not the one or more genes of interest;

(ii) incubating the expression system under conditions that allow expression of the selection marker and the one or more genes of interest; and (iii) selecting for the selection marker, thus identifying the cells that provide for enhanced gene expression.

The enhanced gene expression is achieved by subjecting the cells to a highly stringent selection process due to using the selection marker under the control of an attenuated IRES sequence. The weak IRES sequence results in comparably low expression levels of the selection marker, with the concentration of the selection marker being high enough to survive the selection pressure only in those cells that have a high base expression level. The cells having a high base expression level are however highly efficient when expressing genes not under control of attenuated IRES sequences and provide for enhanced expression of a given gene compared to other cells that lack such high base expression level.

In a still further aspect, the present invention relates to a method of differentially controlling expression of at least two genes of interest comprising the steps of:

(i) generating a panel of mutated IRES sequences by mutating one or more ATG translation initiation site(s) of a wild type IRES sequence;

(ii) testing the strength of the mutated IRES sequence in relation to a wild type IRES sequence;

(iii) selecting a mutated IRES sequence with a strength different from the wild type IRES sequence; and (iv) constructing an expression system comprising a promoter, two or more genes of interest, and the selected mutant IRES, wherein one of the genes of interest is operably linked to the selected mutant IRES, thereby differentially controlling expression of the gene of interest under control of the mutant IRES sequence relative to the gene(s) of interest not under control of the mutant IRES sequence.

The mutated IRES results in decreased expression (translation) of the gene of interest it controls compared to the same or other genes under the control of wildtype IRES sequences or other non-attenuated expression control elements. By selecting the desired mutant (attenuated) IRES sequence, the expression of two or more genes of interest can be finely tuned with respect to each other. This differential control allows construction of expression systems with multiple genes all of which are under control of separate IRES sequences of varying strength, resulting in the possibility to finely tune the ratios of the resulting gene expression products. This is particularly advantageous in case the different genes encode for interacting or complex-forming gene products, more specifically in case the different gene products do not interact in a 1:1 molar ratio.

In yet another aspect, the invention relates to a kit for differential expression of two or more genes of interest comprising: a panel of two or more different IRES sequences for linking to two or more genes of interest, wherein at least one IRES sequence comprises or consists of a nucleotide sequence selected from the group consisting of any one of the nucleotides sequences set forth in SEQ ID Nos. 2-26, wherein each IRES in the panel has a different expression strength allowing construction of expression systems with different ratios of expression products of the two or more genes of interest.

BRIEF DESCRIPTION OF THE DRAWINGS

The invention will be better understood with reference to the detailed description when considered in conjunction with the non-limiting examples and the accompanying drawings.

FIG. 1 shows the relative strength of IRES variants in expressing a gene.

FIG. 2 shows the comparison of non-ATG translation efficiency in cap-dependent and cap-independent translations.

FIG. 3 shows a schematic representation of vectors. (A) Structure of dual-luciferase vectors for determination of IRES variants' strengths. (B) Structures of monoclonal antibody expressing vectors with specified IRES variants applied on the zeocin or DHFR selection genes. (C) Structure of monoclonal antibody expressing vectors with specified IRES variants applied on the LC or HC genes. (D) Amino acid sequences of signal peptide, N- and C-terminal end of LC and HC. CMV, human cytomegalovirus IE gene promoter; mCS, chimeric murine CMV enhancer-simian virus 40 (SV40) promoter; IRESwt, wild type encephalomyocarditis virus (EMCV) internal ribosome entry site (IRES); IRESvn, a specified EMCV IRES variant, n can be 1 to 24; BGHpA, bovine growth hormone polyadenylation signal; SpA, SV40 polyadenylation signal; NPT, neomycin phosphotransferase cDNA; Rluc, renilla luciferase cDNA; Fluc, firefly luciferase cDNA; SPL, light chain signal peptide; LC, light chain cDNA; SPH, heavy chain signal peptide; HC, heavy chain cDNA; DHFR, dihydrofolate reductase cDNA; HP, DNA sequence which contains an additional out-of-frame start codon and has the capacity to form a hairpin structure.

FIG. 6 shows the application of IRES variants for different selection markers to enhance monoclonal antibody (mAb) expression in stable transfections. The relative strength of each IRES variant listed in the table was determined using dual-luciferase vectors in transient transfections as described in FIG. 4. (A) mAb titers in CHO K1 stable transfection pools generated using zeocin as selection marker gene. Each stable transfection pool was generated by transfection of suspension CHO K1 cells with a mAb expressing IRES-mediated tricistronic vector containing specified IRES variants on the zeocin gene (FIG. 3B) and then selected with zeocin for stable transfectants. (B) mAb titers in CHO DG44 stable transfection pools generated using DHFR as selection marker. Each stable transfection pool was generated by transfection of suspension CHO DG44 cells with a mAb expressing IRES-mediated tricistronic vector containing specified IRES variants on the DHFR gene (FIG. 3B). The transfected cells were selected for stable transfectants in medium without containing hypoxanthine and thymine (HT) and then amplified with stepwise increased methotrexate (MTX) concentrations of 50 nM and 250 nM for enhanced mAb titers. Titer of the stable transfection pools were determined in shake flask-batch cultures using a nephelometric method. Each point represents the average and standard deviation of four measurements from two stable transfection pools.

FIG. 10 shows MS/MS spectra of N-terminal tryptic peptides DIQMTQSPSSLSASVGDR (SEQ ID NO:27) of light chain (A) and EVQLVESGGGLVQPGGSLR (SEQ ID NO:28) of heavy chain (B). Matched fragment b- and y-ions are labeled as blue and red, respectively.

DETAILED DESCRIPTION OF THE INVENTION

Figure 4:
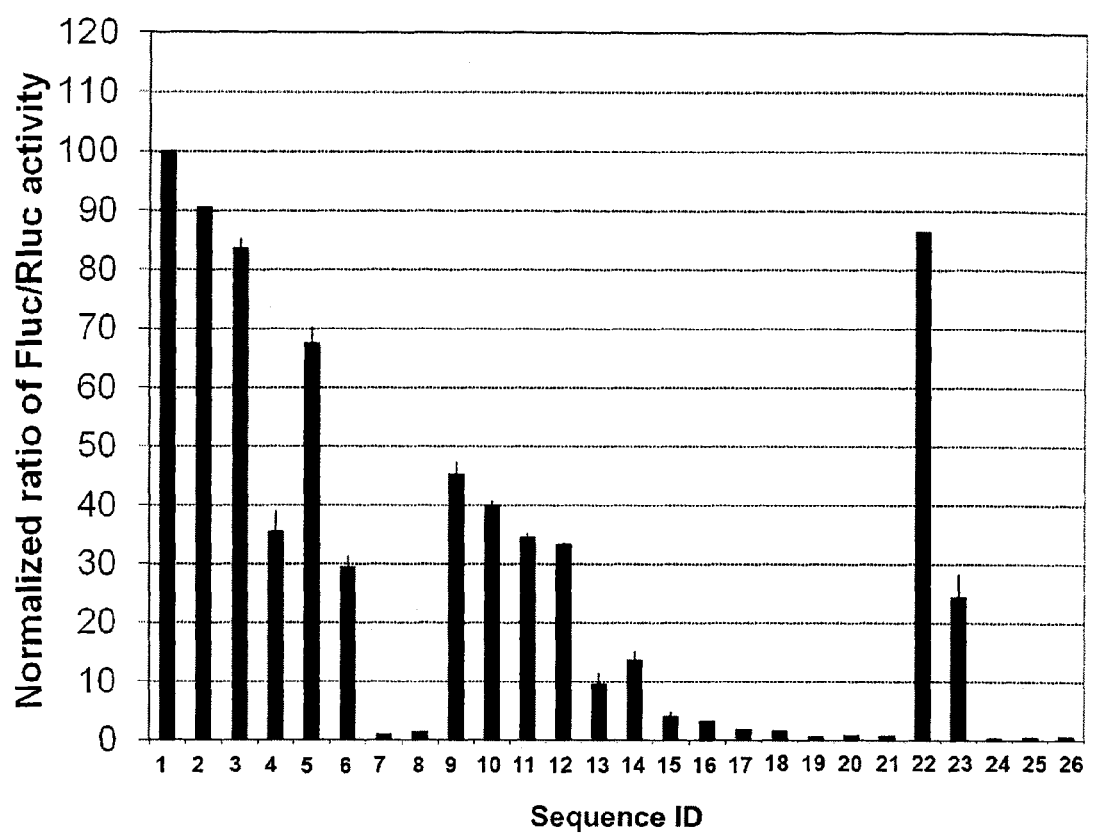
FIG. 4 shows the relative strength of EMCV IRES variants in CHO K1 cells in transient transfections. Equal amounts of dual-luciferase vectors (FIG. 3A) encoding renilla luciferase (Rluc) and firefly luciferase (Fluc) genes were transfected into CHO K1 cells. In each dual-luciferase vector, a specified EMCV IRES variant was applied on the Fluc gene, and the Rluc gene was used to normalize the variation in transfection efficiency. At 48 h post-transfection, cell pellets were collected for analysis of Fluc and Rluc luciferase activities by using Dual-Glo Luciferase Assay Systems and mRNA levels using quantitative real-time PCR (qRT-PCR), respectively. Transfection of each vector was done in duplicates and repeated a second time using independently prepared plasmids and cultures. Ratios of luciferase activities of Fluc to Rluc gene for each IRES variant normalized to the wild-type EMCV IRES. Each bar represents the average and standard deviation of sixteen measurements from four transfections.

The present inventors surprisingly found that the strength of IRES dependent translation can be controlled by deleting or mutating the IRES initiation codons, in particular the 10th, 11th, and 12th ATG/AUG triplet of the Encephalomyocarditis virus (EMCV) IRES. The 10th, 11th, and 12th ATG correspond to positions 568-570, 576-578 and 588-590 of SEQ ID NO:1. Such mutated IRES can subtly control the relative expression of multiple genes over a more than 300-fold range in mammalian cells in both transient and stable transfections. The relative strength of each IRES variant remains similar in different mammalian cell lines and is not gene specific. The control of gene expression by these IRES variants occurs at translational level and the proteins of interest are expressed in the desired size (in contrast to proteins that are translated under the control of 2A elements that may contain undesirable additional amino acid residues as a result of incomplete cleavage).

In a first aspect the invention relates to a nucleic acid molecule comprising a first IRES sequence, wherein the IRES sequence is a mutant IRES sequence and comprises or consists of a nucleotide sequence selected from the group consisting of any one of the nucleotides sequences set forth in SEQ ID Nos. 2-26.

In various embodiments of the invention, the nucleic acid molecule further comprises a nucleotide sequence encoding a gene of interest A, wherein the IRES sequence and the nucleotide sequence encoding a gene of interest A are operably linked.

In still further embodiments, the nucleic acid molecule may comprise a nucleotide sequence encoding a gene of interest B, which may optionally be linked to a second IRES sequences. In addition, a still further nucleotide sequence encoding for a gene of interest C, which may again be optionally linked to a third IRES sequence may be included.

Generally, the nucleic acid molecules described herein may comprise multiple genes of interest, with each of these genes being optionally translationally controlled by a separate IRES sequences. Accordingly, in various embodiments the nucleic acid molecules of the invention may comprise genes of interest A, B and C and optionally one or more further genes (for example designated gene D, E . . . ), wherein each of these genes is operably linked to an IRES sequence, preferably a separate IRES sequence. "Separate IRES sequence", as used in this connection, means that each gene is controlled by its own IRES sequence.

The IRES sequences used for expression control of the genes of interest besides gene A, i.e. the second and/or third and/or any further IRES sequence may be independently selected from the group consisting of wild type IRES sequences or mutant IRES sequences, with the latter preferably differing from a wild type IRES sequence at one or more ATG translation initiation site(s). "Wild type IRES sequence", as used herein, includes, but is not limited to the IRES sequence set forth in SEQ ID NO:1. However, in a preferred embodiment, a given wild type IRES sequence comprises or consists of the nucleotide sequence of SEQ ID NO:1. The mutant IRES sequences used may be defined similarly to the first IRES sequence that is linked to gene A, i.e. may comprise or consist of a nucleotide sequence selected from the group consisting of any one of the nucleotides sequences set forth in SEQ ID Nos. 2-26. Accordingly, in various embodiments, the second and/or third and/or any further IRES sequence comprises or consists of a nucleotide sequence selected from the group consisting of any one of the nucleotides sequences set forth in SEQ ID Nos. 2-26.

In various embodiments, the mutant IRES sequence may comprise a short DNA sequence which contains an additional out-of-frame ATG and has the capacity to form a hairpin structure.

In specific embodiments of tricistronic expression systems, the nucleic acid molecule comprises the genes of interest A, B and C and a first, second and third IRES sequence, and the order of the elements on the coding strand is: 5'-second IRES-gene of interest B-first IRES-gene of interest A-third IRES-gene of interest C-3'. Herein, the separate elements are operably linked, either directly by a direct bond between the respective nucleotide sequences or by means of a suitable linker nucleotide sequence.

In various embodiments of the above-described nucleic acid molecules, the gene of interest A encodes a selection marker. The selection marker may be any gene product that allows for the selection of cells expressing said marker over those not expressing the marker or, in quantitative manner, the selection of those cells expressing marker levels above a given threshold level over those not expressing the marker or expressing it at levels below the threshold level.

The other genes of interest may be any protein or peptide. In various embodiments, the gene of interest B may for example comprise a nucleic acid sequence encoding a light chain of an antibody and/or the gene of interest C comprises a nucleic acid sequence encoding a heavy chain of an antibody.

It is generally preferred that the nucleic acid molecule is a DNA molecule. Accordingly, if any information is given herein with respect to the order or the orientation of the elements disclosed, this always refer to the coding strand of a DNA molecule, if not explicitly indicated otherwise.

In various embodiments, the nucleic acid molecule may be comprised in a vector, preferably a plasmid.

To form a functional expression cassette, the nucleic acid molecule may comprise a promoter that is operably linked to the gene(s) of interest and the IRES sequence(s). This means that the promoter is arranged upstream of all the other elements of the nucleic acid molecule, in particular the genes of interest and the IRES sequences and controls their transcription. Such an expression cassette may additionally comprise downstream elements necessary for expression, such as, for example, a poly-adenylation sequence.

The nucleic acid molecules of the invention may be comprised in a cell. Accordingly, the invention also features host cells comprising the nucleic acid molecule described herein. These cells are preferably recombinant cells. Typically, the cells are eukaryotic, preferably mammalian cells. Suitable mammalian cells may be selected, without limitation, from the group consisting of CHO K1 from Chinese hamster ovary, CHO DG 44 from Chinese hamster ovary, HEK293 from human embryonic kidney, BHK from baby hamster kidney, 3T3 from mouse embryo, and COST from African Green Monkey kidney.

Another aspect of the invention relates to A method of identifying cells that provide for enhanced gene expression comprising the steps of: (i) constructing a cell-based expression system comprising a promoter, a gene encoding for a selection marker, one or more genes of interest different from the selection marker gene, and a mutant IRES sequence that comprises or consists of a nucleotide sequence selected from the group consisting of any one of the nucleotides sequences set forth in SEQ ID Nos. 2-26, wherein the mutant IRES sequence is operably linked to the gene encoding for a selection marker but not the one or more genes of interest; (ii) incubating the expression system under conditions that allow expression of the selection marker and the one or more genes of interest; and (iii) selecting for the selection marker, thus identifying the cells that provide for enhanced gene expression.

As already described above, the enhanced gene expression is achieved by subjecting the cells to a selection process based on the expression of the selection marker. Since the selection marker is under the control of an attenuated IRES sequence, the weak IRES sequence results in comparably low expression levels of the selection marker. By setting a threshold level for the selection marker concentration, only those cells that, despite of being under control of an attenuated IRES sequence, express marker concentrations above the threshold concentration can be identified. These cells are those cells that have a high base expression level and thus are highly efficient when expressing genes under control of non-attenuated regulatory elements and therefore provide for enhanced expression of a given gene compared to other cells that lack such high base expression level. Depending on the type of selection marker used, for example a protein/enzyme that provides for resistance against a cytotoxin, such as an antibody, the threshold level may be the selection marker concentration necessary for cell survival. In such an embodiment, only those cells that survive the selection process are those having sufficiently high base expression levels.

In the selecting step, the selection conditions can be adapted as desired, for example in order to control the stringency of the selection process. For example, in case the selection marker confers resistance to a cytotoxic substance, the concentration of the cytotoxic substance may be increased to increase stringency of the selection process or decreased to decrease the stringency of the selection process. The other alternative or cumulative option to control the stringency of the selection is the selection of the mutant IRES sequence. The more attenuated the IRES sequence is, the higher is the stringency of the selection process.

In various embodiments, the order of the elements on the coding strand is:

5'-promoter-gene of interest-mutant IRES-selection marker-3'

Again, all these elements are operably linked in that they are either directly linked by a direct covalent bond between the respective nucleotide sequences or by means of a suitable linker nucleotide sequence.

In various embodiments, the expression system comprises at least two genes of interest, wherein at least one of said genes of interest is operably linked to an IRES sequence, wherein said IRES sequence is a wildtype IRES sequence or a mutant IRES sequence that differs from a wild type IRES sequence at one or more. ATG translation initiation site(s). The IRES sequence may be defined as the IRES sequence controlling the selection marker expression, but is selected independent from this mutant IRES sequence.

In all embodiments described above, the mutant IRES sequence may comprise a short DNA sequence which contains an additional out-of-frame ATG and has the capacity to form a hairpin structure.

The cells used in the cell-based expression system may preferably be eukaryotic cells, more preferably mammalian cells. The mammalian cells can, without limitation be selected from the group consisting of CHO K1 from Chinese hamster ovary, CHO DG 44 from Chinese hamster ovary, HEK293 from human embryonic kidney, BHK from baby hamster kidney, 3T3 from mouse embryo, and COS7 from African Green Monkey kidney.

The invention also encompasses methods of differentially controlling expression of at least two genes of interest. These methods comprise the steps of:
(i) generating a panel of mutated IRES sequences by mutating one or more ATG translation initiation site(s) of a wild type IRES sequence;
(ii) testing the strength of the mutated IRES sequence in relation to a wild type IRES sequence;
(iii) selecting a mutated IRES sequence with a strength different from the wild type IRES sequence; and
(iv) constructing an expression system comprising a promoter, two or more genes of interest, and the selected mutant IRES, wherein one of the genes of interest is operably linked to the selected mutant IRES, thereby differentially controlling expression of the gene of interest under control of the mutant IRES sequence relative to the gene(s) of interest not under control of the mutant IRES sequence.

In various embodiments of the invention, the method may be limited to methods that only include steps (iii) and (iv), for example in cases where a set of mutated IRES sequences to select from is already available.

The step of generating a panel of mutated IRES sequences, if included, may comprise mutating one or more ATG translation initiation site(s) of a wild type IRES sequence located at the 3' end of said IRES sequence. Suitable mutant IRES sequences that may thus be generated include, but are not limited to those that comprise or consist of any one of the nucleotides sequences set forth in SEQ ID Nos. 2-26.

In various embodiments, the constructed expression system comprises multiple genes of interest, for example 3, 4, 5 or more genes of interest, wherein at least one of the genes of interest is operably linked to the selected mutant IRES sequence. All genes of interest not operably linked to the selected mutant IRES sequence may be operably linked to an IRES sequence different from the selected mutant IRES sequence. This IRES sequence different from the selected mutant IRES sequence may be a wildtype IRES sequence or a mutant IRES sequence. Suitable mutant IRES sequences include those that comprise one or more mutated ATG translation initiation site(s) at the 3' end of said IRES sequence or that comprise or consist of any one of the nucleotides sequences set forth in SEQ ID Nos. 2-26, but are selected such that they are different from the "selected mutant IRES".

Such a method may be used to control or finely tune translation such that agglomeration of the expression products of the two or more genes of interest is minimized. Agglomeration may for example occur if two gene products that interact with each other are expressed in ratios that interfere with or impair the correct interaction resulting in agglomeration. In order to provide for functional gene products, it is usually desirable to avoid such agglomeration. To achieve this in systems where two or more interacting gene products are co-expressed, the described methods can be used.

In various embodiments of such methods, the step of selecting a mutated IRES sequence with a strength different from the wild type IRES sequence includes the steps of:
(i) expressing two genes of interest, wherein one gene of interest is operably linked to one of the mutated IRES sequences;
(ii) quantifying the agglomeration of the expression products of the two genes of interest;
(iii) repeating steps (i) and (ii) for different IRES sequences;
(iv) comparing the agglomeration of the expression products of the two genes of interest for the different IRES sequences used; and
(v) selecting a mutated IRES sequence that results in minimized agglomeration of the expression product of the two genes of interest.

This method can be adapted for more than two genes by subjecting at least two, preferably each, of the genes to translational control by a different element (IRES sequence) and selecting the mutant IRES sequences for the different genes such that agglomeration is minimized. The selection of different attenuated IRES sequences allow fine tuning the translational efficiency and thus the levels of the gene products. By controlling the levels with respect to each other, i.e. the molar ratios of the different gene products, the interaction and/or complex formation can be regulated, allowing in turn to minimize agglomeration.

In various embodiments one gene of interest comprises or consists of a nucleic acid sequence encoding an antibody light chain and/or one gene of interest comprises or consists of a nucleic acid sequence encoding an antibody heavy chain. In case both are present, i.e. one gene of interest comprises/consists of a nucleic acid sequence encoding an antibody light chain and one gene of interest comprises/consists of a nucleic acid sequence encoding an antibody heavy chain, the gene of interest encoding an antibody heavy chain may be operably linked to the selected mutant IRES. This results in reduced expression (translation) of the heavy chain relative to the light chain and promotes correct antibody formation.

In various embodiments, wherein one gene of interest comprises or consists of a nucleic acid sequence encoding an antibody light chain and one gene of interest comprises or consists of a nucleic acid sequence encoding an antibody heavy chain, these two genes are arranged such that the gene encoding the light chain is upstream (i.e. is 5' on the coding strand) of the gene encoding the heavy chain.

In the described methods for differential control of gene expression, the expression system may further comprise a selection marker operably linked to a mutant IRES sequence. Said the mutant IRES sequence comprising one or more mutated ATG translation initiation site(s) at the 3' end of said IRES sequence or comprising or consisting of any one of the nucleotides sequences set forth in SEQ ID Nos. 2-26. By including such a selection marker the above described methods for differential expression control and identification of cells that provide for enhanced gene expression may be combined, as the selection marker provides the possibility to select for those cell-based expression systems, e.g. clones or cell population, that has a sufficiently high base expression level and thus provides for higher yields.

The kits of the invention are useful for differential expression of two or more genes of interest. These kits comprise a panel of two or more different IRES sequences for linking to two or more genes of interest, wherein at least one IRES sequence comprises or consists of a nucleotide sequence selected from the group consisting of any one of the nucleotides sequences set forth in SEQ ID Nos. 2-26, wherein each IRES in the panel has a different expression strength allowing construction of expression systems with different ratios of expression products of the two or more genes of interest. The kit may further include instructions for use. Using these kits, the skilled artisan can construct an expression system comprising two or more genes that are differentially controlled with respect to their expression (translation) by selecting one or more of the IRES sequences provided in the kit, linking those operably to the genes and then expressing the resulting constructs, for example in a cell-based system. The kits may also be used for the identification methods described herein. In such embodiments, the kit may further comprise a nucleotide sequence encoding for a selection marker, optionally already in combination with a mutant IRES sequence, i.e. operably linked thereto. The IRES sequences provided in the kit as well as all other nucleotide sequences that may be contained therein typically have the form of nucleic acid molecules, preferably double stranded nucleic acid molecules. These molecules may have blunt or sticky ends for ligation into a vector of choice. In various embodiments, these molecules may comprise restriction endonucleases sites at one or both ends to allow specific cleavage (to facilitate ligation into a vector). The respective endonucleases needed for cleavage may also be included in the kit. In addition, the kit may include all auxiliaries, such as buffers, typically used and known as such in the field.

The term "expression system", as used herein, relates to vehicles or vectors for the expression of a gene in a host cell or by cell-free expression method (such as a method based on a reticulocyte lysate) as well as vehicles or vectors which mediate stable integration of a gene into the host chromosome. In a preferred embodiment the gene is expressed in a host cell. Such host cell may be a eukaryotic cell such as a yeast cell, an insect cell, a *Pichia Pastoris* cell, a Tobacco cell or a mammalian cell. More preferably, the mammalian cell is selected from the group comprising or consisting of CHO K1 from Chinese hamster ovary, CHO DG 44 from Chinese hamster ovary, HEK293 from human embryonic kidney, BHK from baby hamster kidney, 3T3 from mouse embryo, and COST from African Green Monkey kidney.

The term "vehicle", as used herein, means a construct which is capable of delivering and expressing, one or more gene(s) or sequence(s) of interest in a host cell. Representative examples of such vehicles include, but are not limited to, viral construct such as AAV, non-viral constructs, nucleic acid expression constructs, naked DNA, and certain eukaryotic cells (e.g., producer cells). "Vectors" are understood for purposes herein as elements, made up of nucleic acids, that contain a nucleic acid contemplated herein as a characterizing nucleic acid region. They enable said nucleic acid to be established as a stable genetic element in a species or a cell line over multiple generations or cell divisions. In the context herein, a nucleic acid as contemplated herein is cloned into a vector. Included among the vectors are, for example, plasmids, viral vectors and cosmids. Using the further genetic elements present in each case, vectors are capable of establishing themselves as stable units in the relevant host cells over multiple generations. They can be present extrachromosomally as separate units, or can be integrated into a chromosome resp. into chromosomal DNA. The term "plasmid", as used herein, relates to a small DNA molecule that is physically separate from, and can replicate independently of, chromosomal DNA within a cell. Most commonly plasmids are small circular, double-stranded DNA molecules in bacteria or eukaryotes and may be of natural or artificial origin. In preferred embodiments of the present invention, said plasmids are mammalian expression vectors that are well-known in the art.

"Cell-free expression", as used herein, relates to methods using protein-based transcription and translation that is not carried out in a viable cell. Such cell-free expression methods may include, but without being limited to, methods based on reticulocyte lysate or wheat germ.

The terms "promoter" or "promoter nucleotide sequence", as interchangeably used herein, relates to a region of DNA or RNA that initiates transcription of a particular gene. Promoters are located near the Transcription Start Sites of genes, on the same strand and upstream on the nucleotide (towards the 3' region of the anti-sense strand, also called template strand and non-coding strand). Promoters can be about 100-1000 base pairs long.

As used herein, the term "operably linked" means that a nucleic acid sequence or a gene and an expression control sequence such as a promoter are positioned in such a way that the expression control sequence directs the expression of the nucleic acid sequence or gene when the appropriate molecules such as transcriptional activator proteins are bound to the expression control sequence.

As used herein, the term "gene of interest" refers to a nucleic acid sequence comprising the coding sequence for the gene of interest which can be either spaced by introns or which is a cDNA encoding the open reading frame. Typically, the term "gene of interest" refers to a nucleic acid sequence further comprising a polyadenylation signal sequence. Preferably, the gene of interest can be transcribed into a RNA having catalytic activity (such as ribozymes) or can be transcribed and translated into a peptide or protein.

The term "selection marker", as used herein, relates to a gene introduced into a cell, especially to cells in culture that confers a trait suitable for artificial selection. They are a reporter gene used to indicate the success of a transfection or other procedure meant to introduce foreign DNA into a cell. Selectable markers for mammalian cells may include, but are not limited to, genes that mediate resistance to methotrexate (such as the dihydrofolate reductase (DHFR)), zeocin, neomycin, hygromycin, puromycin and blasticidin.

"Internal ribosomal entry site" or "IRES", as interchangeably used herein, relates to a nucleotide sequence that allows for translation initiation in the middle of a messenger RNA (mRNA) sequence as part of the greater process of protein synthesis. Usually, in eukaryotes, translation can be initiated only at the 5' end of the mRNA molecule, since a 5' cap recognition is required for the assembly of the initiation complex. The location for these sites is often in the 5'UTR. A preferred IRES of the present invention is an IRES isolated from the Encephalomyocarditis virus. In more preferred embodiments, this IRES is set forth in SEQ ID NO:1. In various embodiments of the invention, the 10th, 11th, and 12th of the ATG/AUG triplet of the Encephalomyocarditis virus (EMCV) IRES of SEQ ID NO:1 are mutated. The 10th ATG corresponds to positions 568-570 of SEQ ID NO:1. The 11th ATG corresponds to positions 576-578 of SEQ ID NO:1. The 12th ATG corresponds to positions 588-590 of SEQ ID NO:1.

The term "ATG translation site" or "start codon", as interchangeably used herein, relates to the first codon of a messenger RNA (mRNA) transcript that is translated by a ribosome. The start codon always codes for methionine in eukaryotes and a modified Met (fMet) in prokaryotes. The most common start codon is ATG on DNA level or AUG on RNA level. The start codon is often preceded by a 5' untranslated region (5' UTR). In prokaryotes this includes the ribosome binding site. Alternative start codons are different from the standard AUG codon and are found in both prokaryotes (bacteria) and eukaryotes. Alternate start codons are still translated as Met when they are at the start of a protein (even if the codon encodes a different amino acid otherwise) due to a separate transfer RNA (tRNA) that is used for initiation.

The terms "increased expression" or "reduced expression", as used herein, relate to a detectable and significant reduction or increase of expression of a gene of interest or a selection marker that comprise an IRES sequence that is different from a wild type IRES sequence compared to the expression of the same gene or selection marker that is linked to the wild type sequence of the above described IRES. When the expression of a gene linked to a mutated IRES and the expression of the same gene linked to the wild type IRES are compared other parameters such as cell type, medium, temperature, expression time, $CO_2$ atmosphere are not changed.

The terms "wild type" or "wild type sequence", as used herein, relate to a nucleotide sequence that is different from a nucleotide sequence that contains one or more mutations. This means that the term "wild type sequence" may refer to the nucleotide or nucleotide sequence that is found in the majority of individuals. In this context, majority can be understood as the genetic variant with the highest frequency in a representative group of individuals. Such representative group may represent the overall population, or may be a group representing individuals that have been selected based on their genetic background, age, gender, weight, family's disease history and/or other parameters. However, the term "wild type sequence" may also refer to the genotype of the typical form of a species as it occurs in nature and that is not related to a pathological condition and/or loss of function. In the context of a specific genetic locus, the term "mutation" or "mutated", as used herein, relates to any nucleotide or nucleotide sequence that is different from the wild type sequence. In preferred, embodiments of the present invention, the mutant and the wild type may vary from each other by having at least 40%, 50%, 60%, 70%, 75%, 80%, 85%, 90%, 95% or 99% sequence identity. As used herein, "sequence identity" or "identity" in the context of two nucleic acid or peptide sequences makes reference to the residues in the two sequences that are the same position when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "mutation", as used herein, also relates to a change introduced into a parental sequence that concerns one or more nucleotides, including substitutions, insertions or deletions (including truncations). The consequences of a mutation may include, but are not limited to, the creation of a new character, property, function, phenotype or trait not found in the protein encoded by the parental sequence. The term "deletion", as used herein, relates to a mutation in which a part of a chromosome or a sequence of DNA or RNA is missing. Deletion is the loss of genetic material. Any number of nucleotides can be deleted, from a single base to an entire piece of chromosome. Deletions can be caused by errors in chromosomal crossover during meiosis. In contrast, the term "insertion", as used herein, refers to the addition of one or more nucleotide bases or base pairs into an RNA or DNA sequence. This can often happen in microsatellite regions due to the DNA polymerase slipping. Insertions can be anywhere in size from one base pair incorrectly inserted into a DNA sequence to a section of one chromosome inserted into another. The term "deletion of the ATG translation initiation site", as used herein, means that all three nucleotide of the ATG codon are deleted.

In one specific example, the mutation is a point mutation, i.e. the replacement of one or more nucleotides and/or amino acids in a given sequence. It is understood that if the term "mutation" is used in relation to a protein sequence, that the nucleotide sequence encoding the protein can comprise multiple mutations or modifications, including silent mutations that, for example, serve the purpose to increase expression efficiency (codon-optimization) without changing the amino acid sequence. In preferred embodiments, the mutations, e.g., silent mutations change the expression and/or secretion efficiency of the peptide or protein encoded by the nucleic acid molecule. Coding or non-coding sequence stretches may be subjected to mutagenesis. The mutagenesis of non-coding sequences may be advantageous, e.g., for the achievement of an improved expression and/or secretion of a peptide or protein encoded by a different sequence stretch within the nucleic acid molecule.

The term "mutagenesis", as used herein, means that the experimental conditions are chosen such that nucleotide bases controlling protein expression are changed or that the amino acid naturally occurring at a given sequence position of a protein sequence can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, an initial translation site ATG codon is changed to a non-ATG codon or that one amino acid at a chosen sequence position is replaced by a stretch of three random mutations, leading to an insertion of two amino acid residues compared to the length of the respective segment of the wild type protein. Such an insertion or deletion may be introduced independently from each other in any of the peptide segments that can be subjected to mutagenesis in the invention.

"Codon-optimized" means that codons encoding one amino acid residue are replaced by a different codon encoding the same amino acid, but being more frequently used by a given host organism for this particular amino acid. It is understood that such nucleotide sequences that encode a homologous polypeptide may have high sequence variability so that sequence identity between the nucleic acid molecules encoding the same or homologous polypeptides may be low.

The natural coding sequence of a protein sequence, i.e. the respective gene segment of an enzyme, can be used as a starting point for the mutagenesis of the amino acid positions selected in the present invention. For the mutagenesis of the recited amino acid positions, the person skilled in the art has at his disposal the various established standard methods for site-directed mutagenesis (Sambrook, J. et al. (2001) Molecular Cloning: A Laboratory Manual, 3rd Ed., Cold Spring Harbor Laboratory Press, Cold Spring Harbor, N.Y.). A commonly used technique is the introduction of mutations by means of PCR (polymerase chain reaction) using mixtures of synthetic oligonucleotides, which bear a degenerate base composition at the desired sequence positions. For example, use of the codon NNK or NNS (wherein N=adenine, guanine, cytosine or thymine; K=guanine or thymine; S=adenine or cytosine) allows incorporation of all 20 amino acids plus the amber stop codon during mutagenesis, whereas the codon VVS limits the number of possibly incorporated amino acids to 12, since it excludes the amino acids Cys, Ile, Leu, Met, Phe, Trp, Tyr, Val from being incorporated into the selected position of the polypeptide sequence (V=adenine, guanine, or cytosine); use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. Another possibility is the use of codons NDT or NDC (wherein D=adenine, guanine, or thymine) as this provides a 1:1 ratio between the number of codons and the encoded amino acids, thus reduces the screening effort, and leads to a balanced set of 12 polar, non-polar, aromatic, non-aromatic, hydrophilic and hydrophobic amino acid residues (Arg, Asn, Asp, Cys, Gly, His, Ile, Leu, Phe, Ser, Tyr, Val [Reetz M T et al., 2008, ChemBioChem, 21; 9(11):1797-804]). "Testing the strength of an mutated IRES" refers to methods that allow qualitative or quantitative testing of the strength of the mutation. Usually, the strength of the mutated IRES is tested by quantification of the gene product that is expressed from the gene that is linked to the mutated IRES. In case the mutated IRES is linked to a selection marker, said strength may be tested by quantification of the gene product of another gene that was brought into a host cell together with the selection marker.

"At least one", as used herein, relates to one or more, in particular 1, 2, 3, 4, 5, 6, 7, 8, 9, 10 or more.

The term "sequence", as used herein, relates to the primary nucleotide sequence of nucleic acid molecules.

The term "3' end" or "3'hydroxyl end" as interchangeably used herein relates to the termination at the hydroxyl group of the third carbon in the sugar-ring of a nucleic acid molecule, and is also known as the tail end. The term "5' end" or "5'phosphate end" as interchangeably used herein designates the end of the DNA or RNA strand that has a phosphate group at the fifth carbon in the sugar-ring of the deoxyribose or ribose at its terminus.

"Hairpin structure", as used herein, relates to an intramolecular stem-loop base pairing that can occur in single-stranded DNA or, more commonly, in RNA. It occurs when two base pair regions of the same strand, usually complementary in nucleotide sequence when read in opposite directions, form a double helix that ends in an unpaired loop. The resulting structure is a key building block of many RNA secondary structures.

"Antibody", also known as an immunoglobulin (Ig), as used herein relates to a large Y-shaped protein that is used by the immune system to identify and neutralize foreign objects such as bacteria and viruses. Antibodies are typically made of basic structural units—each with two large heavy chains and two small light chains. There are several different types of antibody heavy chains, and several different kinds of antibodies, which are grouped into different immunoglobulin isotypes based on which heavy chain they possess. Five different antibody isotypes are known in mammals, which perform different roles, and help direct the appropriate immune response for each different type of foreign object they encounter. In a preferred embodiment of the present invention, the recombinantly expressed protein is an IgG. Antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end, a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "enhancing gene expression", as used herein, means that the amount of a protein of interest expressed in a host organism containing a vector or integrated DNA sequence comprising a gene of interest and a selection marker wherein the selection marker is under the control of a mutated IRES is increased compared to the amount of the same protein expressed in the same host containing the same vector or integrated DNA sequence comprising the same gene of interest and the same selection marker wherein the selection marker is under the control of a wild type IRES.

"Culturing", "cultivating" or "cultivation", as used herein, relates to the growth of cells in a specially prepared culture medium under supervised conditions. The term "conditions suitable for (recombinant) expression" relates to conditions that allow for production of the protein of interest in cells using methods known in the art, wherein the cells are cultivated under defined media and temperature. In this context, $CO_2$ conditions may be used which are known in the art or, optionally, the cell may be cultivated under $CO_2$-free conditions (e.g. MOPS buffer). The medium may be a nutrient, minimal, selective, differential, transport or enriched medium. Preferably, the medium is a nutrient medium. Growth and expression temperature of the mammalian host cell may range from 25° C. to 45° C. Preferably, the growth and expression temperature range from 30° C. to 37° C. The $CO_2$ culture and expression conditions may range from 2% to 15%. Preferably, the $CO_2$ culture and expression conditions range from 5% to 10%. Optionally, the $CO_2$ concentration can be dependent on the pH of the culture media, particularly when bioreactor cultivation is used. Conditions for such bioreactor cultivation are known in the art and comprise a pH ranging from 6.5 to 7.5.

In specific embodiments, the recombinantly expressed protein of interest can be purified by methods known in the art. These methods include, but are not limited to chromatography or ultracentrifugation. In this context, the term "isolated" means that the protein of interest is purified to the extent that substantially at least 60%, 70%, 75%, 80%, 85%, 90%, 95% or 100% (in terms of weight or molar percentage) are the protein of interest compared to unintended contamination (such as other proteins, lipids, sugars, metabolic compounds of the host cell).

The term "selecting for the selectable marker", as used herein, means that a compound whose influence on cells can be neutralized by the selection marker is applied at a concentration on the cell that allows differentiating whether the selection marker is present in the cell at relatively high or relatively low concentration. In the preferred embodiments, the differentiation between relatively low and high expressing cells is done via their viability.

The term "differentially controlling translation of a (first) gene of interest", as used herein, relates to increased or reduced expression of this gene of interest compared to a previously determined expression rate under the same expression conditions or to the expression of a second, third, fourth etc. gene of interest that is expressed in parallel to the first gene of interest.

"Kit", as used herein, relates to a kit-of-parts wherein the separate components of the kit are physically separated as individual components.

The term "protein interaction", as used herein, relates to intentional physical contacts established between two or more proteins as a result of biochemical events and/or electrostatic forces. Protein complex assembly can result in the formation of homo-oligomeric or hetero-oligomeric complexes. In addition to the conventional complexes, as enzyme-inhibitor and antibody-antigen, interactions can also be established between domain-domain and domain-peptide. Moreover, interactions can be classified into stable or transient, and also according to the nature of the chemical bonds established between proteins. Methods to investigate protein-protein interactions include, but are limited to, yeast-two-hybrid assay, mass spectrometry based assays, co-immunoprecipitation, protein microarrays, analytical ultracentrifugation, light scattering, fluorescence spectroscopy, luminescence-based mammalian interactome mapping (LUMIER), resonance-energy transfer systems, mammalian protein-protein interaction trap, surface plasmon resonance, protein-fragment complementation assay, and calorimetry.

The term "nucleic acid molecule" or "nucleic acid sequence", as used herein, relates to DNA (deoxyribonucleic acid) or RNA (ribonucleic acid) molecules. Said molecules may appear independent of their natural genetic context and/or background. The term "nucleic acid molecule/sequence" further refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms.

The term "panel", as used herein, refers to a plurality of nucleotides comprising IRES. In certain embodiments, the panel comprises wild type and mutant IRES. In certain embodiments, the panels comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 IRES. In certain embodiments, the panels comprise from 5-10 IRES, 10-15 IRES, 15-20 IRES, 20-25 IRES or more.

The terms "(protein) agglomeration" or "(protein) aggregation", as interchangeably used herein, relate to a biological phenomenon in which mis-folded proteins aggregate (i.e., accumulate and clump together) either intra- or extracellularly. These protein aggregates may be insoluble and the aggregated proteins may lose their function, e.g. they lose their specific binding capacity or localization or they lose their enzymatic activity. Sometimes aggregated proteins are often toxic, i.e. protein aggregates have been implicated in a wide variety of disease known as amyloidoses, including ALS, Alzheimer's, Parkinson's and prion disease. Methods to detect protein agglomeration are well-known in the art and basically comprise all methods that allow the detection of protein/protein interaction or protein localization, such as, but not limited to size-exclusion chromatography, co-immunoprecipitation, bimolecular fluorescence complementation (BiFC), affinity electrophoresis, label transfer, in-vivo crosslinking of protein complexes, tandem affinity purification (TAP), chemical cross-linking, proximity ligation assay (PLA), Bio-Layer Interferometry, dual polarisation interferometry (DPI), static light scattering (SLS), dynamic light scattering (DLS), surface plasmon resonance, fluorescence polarization/anisotropy, fluorescence resonance energy transfer (FRET), NMR, Isothermal Titration calorimetry (ITC) and Microscale Thermophoresis (MST). In other embodiments, the agglomeration can be detected by loss-of-function assays that are specific to the protein of interest. In further embodiments, the agglomeration of antibodies is detected by size-exclusion chromatography.

In specific embodiments of the invention, the nucleic acid molecules can comprise a nucleic acid sequence encoding for a gene of interest and/or sequences that allow its insertion into a vector, and can be cloned in a known host organism. Several cloning techniques, including amplification of nucleic acids, their restriction by according enzymes, purification and ligation, and transformation techniques, are known in the art and described in more detail by Sambrook et al. [Sambrook, J. et al. (1989) Molecular Cloning: A Laboratory Manual, 2nd Ed., Cold Spring Harbor Laboratory Press, Cold Spring Harbor, N.Y.]. The produced nucleic acid constructs are verified by sequencing. Sequencing of the nucleic acid constructs can be done by the chain termination method, Sanger sequencing or Maxam-Gilbert sequencing or any other technique known in the art. Alternatively, high-throughput sequencing, like pyrosequencing, SOLiD sequencing or DNA nanoball sequencing, is used to determine the sequence of the nucleic acid molecules of the present invention [Alphey, L. (1997) DNA Sequencing: From Experimental Methods to Bioinformatics, 1st Ed., Bios Scientific Pub Ltd., Oxford, UK].

Based on the above, the skilled person will recognize that the mutated IRES of the present invention can subtly control the relative expression of multiple genes over a more than 300-fold range in mammalian cells in both transient and stable transfections. Further, the present set of mutated IRES provides IRES mutants that cover the whole 300-fold expression range without having "gaps" (meaning that a certain range of expression strength is not covered by the IRES mutants). Thus, the set of IRES mutants of the present invention allow for the first time the fine-tuned expression of a gene of interest or the fine-tuned differential expression of at least two genes of interest.

EXAMPLES

Materials and Methods
Cell Culture and Media
Adherent CHO K1, HEK293, BHK, 3T3, and COST cells (ATCC, Manassas, Va.) were grown in the Dulbecco's modified Eagle's medium (DMEM)+GlutaMax™ (Life Technologies, Carlsbad, Calif.) supplemented with 10% fetal bovine serum (Sigma, St. Louis, Mo.) in a static humidified incubator with 5% $CO_2$ at 37° C. Routine subculture was conducted every 3-4 days by detaching cells with 0.05% trypsin (Life Technologies) and diluting in 20 mL of fresh medium to 2×105 cells/mL in 75 cm2 T-flasks (TPP Techno Plastic Products AG, Switzerland). Suspension CHO K1 cells were obtained by in-house adaptation of adherent CHO K1 (ATCC) into a protein-free medium consisting of 50% HyQ PF (HyClone, Logan, Utah) and 50% CD CHO (Life Technologies) supplemented with 1 g/L sodium carbonate (Sigma), 6 mM glutamine (Sigma), and 0.1% Pluronic F-68 (Life Technologies). Suspension dihydrofolate reductase (DHFR)-deficient CHO DG44 cells (Life Technologies) were grown in protein-free medium supplemented with 1% hypoxanthine and thymine (HT) (Life Technologies). Both suspension CHO K1 and DG44 were maintained in a humidified Kuner shaker (Adolf Kühner AG, Birsfelden, Switzerland) with 8% CO2 at 37° C. Routine subculture was conducted every 3 to 4 days by diluting cells into 25 mL of fresh medium to 2×105 cells/mL in 125 cm3 shake flasks (Corning). Cell density and viability were determined by using the trypan blue exclusion method on an automated Cedex counter (Innovatis, Bielefeld, Germany).

Generation of EMCV IRES Variants
The IRESwt with sequence corresponding to the region from 260 to 848 in the EMCV-R genome (Genebank: M81861) was cloned from the pIRES2-DsRed vector (Clontech Laboratories, CA). Two mutations exist in IRESwt compared to the sequence deposited in the Genebank: mutation of G at 739 to A and insertion of one A after 769. The mutated EMCV IRES variants were generated by either mutation of ATG-10, ATG-11, and ATG-12 individually or in combination to GTG, CTG, ACG, ATA, TTG, or deletion of ATG-11 and ATG-12 and surrounding sequence, or both (FIG. 1). The mutations were obtained by using synthetic primers containing specified mutations during PCR amplification.

Vector Constructions
The dual-luciferase IRES-mediated bicistronic vectors for evaluating the strength of IRES variants in expressing a gene were constructed based on a previously described dual-luciferase vector which expresses renilla luciferase (Rluc) and firefly luciferase (Flue) using two human cytomegalovirus IE gene promoters (CMV) [Yang, Y. S. et al. (2009) Biotechnology and Bioengineering, 102, 1152-1160] (FIG. 3A). The first CMV was replaced with a chimeric murine CMV enhancer-SV40 promoter (mCS) and the Rluc-BGHpA-CMV region was replaced with a specified IRES variant (IRESvn). The IRES-mediated tricistronic vectors containing different IRES variants on zeocin or DHFR were constructed by replacing the CMV and IRESatt-NPT region of a previously described tricistronic vector [Ho, S. C. L. et al. (2012) Journal of Biotechnology, 157, 130-139] with the mCS and IRESvn-Zeocin or IRESvn-DHFR, respectively (FIG. 3B). Zeocin and DHFR cDNAs were cloned from the pcDNA3.1 vector (Life Technologies) and the pSV2-DHFR vector (ATCC, Manassas, Va.), respectively. The IRES-mediated tricistronic vectors containing different IRES variants on LC and HC were constructed by replacing the IRESvn-DHFR-SpA region in a tricistronic vector as described in FIG. 3B with only a SpA sequence, followed by replacing LC with IRESvn-LC and IRESwt-HC with IRESvn-HC respectively, and then insertion of HP-DHFR between the mCS promoter and the first IRES (FIG. 3C). HP is a short DNA sequence which contains an additional out-of-frame ATG and has the capacity to form a hairpin structure [de Quinto, S. L. and Martinez-Salas, E. (1998) Gene, 217, 51-56]. IRESvn-Zeocin, IRESvn-DHFR, IRESvn-LC, and IRESvn-HC were synthesized by overlapping PCR. The last ATG or non-ATG triplet in IRESvn was used as the start codon of the downstream gene. All restriction enzymes used were purchased from New England Biolabs (Ipswich, Mass., USA).

Transient Transfection to Determine the Strength of EMCV IRES Variants

Transient transfections for evaluating the strength of IRES variants in different mammalian cell lines were carried out in 6-well tissue culture plate (NUNC™, Roskilde, Denmark) using Fugene 6 (Roche, Indianapolis, Ind.). 24 h prior to transfection, 2 mL of exponentially growing cells at a cell density of $3 \times 10^5$ cells/mL were seeded into each well of the 6-well plates. Transfection of cultures in each well with the appropriate dual-luciferase vector was done in duplicates using a recipe of 6 µL of Fugene 6: 2 µg of DNA. At 48 h post-transfection, cells were detached with trypsin and analyzed for Rluc and Fluc activities using Dual-Glo Luciferase Assay system (Promega, Madison, Wis.) as described by Yang, Y. S. et al. [Yang, Y. S. et al. (2009) Biotechnology and Bioengineering, 102, 1152-1160]. Each experiment was repeated once by using independently prepared plasmids and cultures. The strength of each IRES variant was calculated as the ratios of luciferase activities of Fluc to Rluc and then normalized to the control, IRESwt.

RNA Extraction and Quantitative Real-Time PCR (qRT-PCR)

Total RNA was isolated from cells transfected with the dual-luciferase vectors at 48 h post-transfection using a RNeasy® Mini Kit (Qiagen, Valencia, Calif.) according to manufacturer's instructions. The Rluc and Fluc mRNA levels were then analyzed using a two-step qRT-PCR protocol. Briefly, 100 ng of RNA were reversely transcribed into cDNA using the ImProm II™ reverse Transcription System (Promega, Madison, Wis.) in a 40 µL reaction. These cDNA samples were analyzed on an iQ-5 Real-time PCR System (Bio-Rad Laboratories, Hercules, Calif.) using a recipe of 10.0 µl of SsoFast™ Evagreen® Supermix (Bio-Rad), 500 nM (final concentration) of forward and reverse primers (Research Biolabs, Singapore) for a specific gene, 2.0 µl of above synthesized cDNA, and 4 µl of HPLC water (Merck, San Diego, Calif., USA) for a 20 µl reaction. Four RNA samples from four independently transfected cultures were analyzed and duplicate measurements were done on each samples. The collected threshold cycle (Ct) values were analyzed using a 2-ΔΔCt method [Livak, K. J. and Schmittgen, T. D. (2001) Methods, 25, 402-408]. ΔCt represents the difference between Ct values of Fluc gene and Rluc gene for IRESwt or a specified IRES variant, and ΔΔCt represents the difference between ΔCt of a specified IRES variant and the control, IRESwt. The 2-ΔΔCt value will be the fold change in mRNA level of the Fluc gene normalized to the Rluc gene for each IRES variant and relative to the IRESwt.

Generation of Stably Transfected mAb Producing Cell Lines

Stably transfected CHO K1 mAb producing cell lines were generated by transfection of suspension CHO K1 cells with the IRES-mediated tricistronic vectors containing Zeocin as the selection marker (FIG. 3B) using electroporation on a Nucleofector (Lonza, Cologne, Germany). In each transfection, $1 \times 10^7$ cells were transfected with 5 µg of linearized plasmids. The transfected cells were then resuspended in 2 mL of protein-free medium preloaded in 6-well suspension culture plates (NUNC™). At 24 h post-transfection, they were collected by centrifuge at 1000 rpm for 5 minutes, and then resuspended in 15 mL of selection medium consisting of protein-free medium supplemented with 600 µg/mL of zeocin (Life Technologies) in 125 mL shake flasks. Selection was continued for two to three weeks by passaging in selection medium every 3 to 4 days until cell viabilities recovered over 95%. Stably transfected CHO DG44 mAb producing cell lines were generated by transfection of suspension CHO DG44 cells with the IRES-mediated tricistronic vectors containing DHFR as the selection marker (FIGS. 3B and 3C). The transfection protocol was the same as described for CHO K1 cells except that the transfected cells were resuspended in 2 mL of HT containing protein-free medium for 24 h recovery after transfection. Selection of stable transfectants was first carried out using protein-free medium without HT and then followed by gene amplification in protein-free medium containing stepwise increased concentrations of methotrexate (MTX) at 50 nM and 250 nM. Selection of each step required around 2 to 3 weeks and was deemed complete when cell viabilities recovered over 95%. To determine the productivity of mAb in stable transfection pools, 25 mL of cultures at a cell density of $2 \times 10^5$ cells/mL were seeded into 125 mL shake flask. Cell density and viability were monitored using Cedex counter until viability dropped below 50%. Supernatant was collected at the end of culture and analyzed for mAb concentration using either a nephelometric method on an IMMAGE 800 immunochemistry system (Beckman Coulter, Buckinghamshire, England) which can quantify mAb with concentrations greater than 9.26 mg/L or enzyme-linked immunosorbent assay (ELISA) when mAb concentrations were less than 9.26 mg/L. Both methods utilized anti-human Fc region antibodies for IgG detection. Operation of the IMMAGE 800 immunochemistry system was according to manufacturer's instructions. ELISA was performed as described by described by Yang, Y. S. et al. [Yang, Y. S. et al. (2009) Biotechnology and Bioengineering, 102, 1152-1160] using affinity purified goat anti-human IgA+IgG+IgM (HC+LC) (KPL, Gaithersburg, Md.) for capture of mAb in the sample and goat anti-human IgG (Fc specific) conjugated to alkaline phosphatase (Sigma-Aldrich) for detection of mAb.

ELISA Analysis of Intracellular Polypeptides to Determine LC:HC Ratios

The LC:HC ratios of intracellular polypeptides in stable transfection pools generated using tricistronic vectors containing different IRES variants on LC and HC (FIG. 3C) were determined using ELISA as described by Ho, S. C. L. et al. [Ho, S. C. L. et al. (2012) Journal of Biotechnology, 157, 130-139]. $1 \times 10^7$ cells were collected from 125 mL shake flask batch cultures growing at exponential phase. They were washed with 1×PBS (1st Base, Singapore) and lysed in RIPA buffer (Thermo Scientific, Waltham, Mass.) supplemented with ProteoBlock protease inhibitor cocktail (Fermentas, Thermo Scientific). The cell lysates were centrifuged at ~1800×g for 30 min at 4° C. The supernatants were then collected and quantified for concentrations of LC and HC polypeptides using alkaline phosphatase-conjugated goat anti-human IgG (Fc specific) for HC detection and goat anti-human IgG (LC specific) for LC detection, respectively. Both detection antibodies were purchased from Sigma-Aldrich. The intracellular LC:HC polypeptide ratio in each stable transfection pool was determined as the measured LC concentration divided by the HC concentration.

Western Blotting of Cell Lysates and Supernatant

Western blotting analyses were carried out to analyze the cell lysates prepared for ELISA under reducing conditions. The concentrations of total proteins in cell lysates were quantified using a BCA protein assay kit (Pierce, Rockford, Ill.). 10 µg of proteins were mixed with NuPAGE loading buffer and NuPAGE reducing buffer (both from Life Technologies) as required, heated at 70° C. for 10 min, and then separated on NuPAGE 4-12% Bis-Tris gels (Life Technologies). Precision plus protein dual-color standards (Bio-Rad Laboratories) was used as molecular weight ladder and to check for membrane transfer. Electrophoresis was run at 200 V for 35 min using MES buffer (Life Technologies). Proteins were transferred to polyvinylidene difluoride (PVDF) membranes using the iBlot system (Life Technologies). The membranes were then blocked in 5% (w/v) blocking milk (Bio-Rad Laboratories) in TBS (1st BASE) containing 0.1% Tween 20 (Promega, Madison, Wis.) for 1 h at room temperature, followed by overnight incubation in HRP conjugated goat anti-human IgG Fc antibody (1:5000 dilution; Bethyl Laboratories, Montgomery, Tex.) and HRP conjugated goat anti-human IgG Kappa LC antibody (1:20000 dilution; Bethyl Laboratories). Protein detection was done using ECL Prime (Amersham-GE Healthcare Life Sciences, Piscataway, N.J.) and exposed on Lumi-Film Chemiluminescent Detection Film (Roche Applied Science, Indianapolis, Ind.).

Same western blotting protocol was used to analyze the culture supernatant collected from stable transfection pools at different LC:HC ratios. The supernatants were collected at the end of culture and analyzed under both reducing and non-reducing conditions. The sample loaded into each lane contained 1 ng of mAb as determined by ELISA using Fc-specific detection antibodies. 10 pg of product was loaded for the sample with LC:HC of 21.24 to prevent overexposure due to the high levels of accumulated LC. HRP conjugated goat anti-human IgG Fc antibody (1:2000 dilution; Bethyl Laboratories) and HRP conjugated goat anti-human IgG Kappa LC antibody (1:5000 dilution; Bethyl Laboratories) were used for primary antibodies.

Purification of mAb Using Protein A Column mAb in the supernatant collected at the end of culture in stable transfection pools at different LC:HC ratios was purified using protein A column on a GE AKTA explorer 100 (GE Healthcare, Uppsala, Sweden). Culture supernatant was loaded on a Tricorn 5/150 Protein A column packed with Mab Select SuRe (GE Healthcare) at a flow rate of 3 mL/min. The column was washed with a terminator buffer consisting of 2 M sodium chloride (Merck, Darmstadt, Germany), 250 mM imidazole (Merck), 10 mM EDTA (Sigma-Aldrich), 4 M urea (Sigma-Aldrich) at pH 7.0, and then followed by an elution buffer of 100 mM acetate (Sigma-Aldrich) and 100 mM arginine (Sigma-Aldrich) at pH 3.5. Eluted samples were neutralized using 1 M Tris (Sigma-Aldrich). The column was regenerated using 0.1 M glycine (Merck) at pH 2.5.

NanoLC-MS/MS Analysis to Measure Signal Peptide Cleavage

Protein A purified mAb in stable transfection pools at different LC:HC ratios were analyzed for the signal peptide cleavage sites using NanoLC-MS/MS. Briefly, 2 µg of purified mAb was diluted with 2× Laemmli buffer (62.5 mM Tris-HCl, pH 6.8, 25% glycerol, 2% SDS, 0.01% Bromophenol Blue, 25 mM DTT), heated at 95° C. for 10 min, separated by Bio-Rad Mini-PROTEAN® TGX™ precast gels (4-15%) for 30 min at 200 v, and stained with 0.1% Coomassie blue R250 in 50% Methanol, 10% acetic acid, 40% $H_2O$ (V/V). After destaining, the gel bands for heavy chain and light chain were excised, washed with 25 mM ammonium bicarbonate-50% acetonitrile and dehydrated with acetonitrile, reduced with 25 mM DTT in 50 mM ammonium bicarbonate at 56° C. for 25 min, and alkylated with 55 mM iodoacetamide at room temperature in the dark for 30 min. After dehydration, gel plugs were digested with 10 ng/µl mass spectrometry grade trypsin gold (Progema) in 25 mM ammonium bicarbonate at 37° C. overnight. Peptides were extracted first with 20 mM ammonium bicarbonate, then with 50% acetonitrile, 5% formic acid in H2O, evaporated to dry in SpeedVac (Savant Savant Instruments, Holbrook, N.Y., USA), and resuspended with 10 µl 2% methanol-1% formic acid.

Nanoscale liquid chromatography (NanoLC) was performed on nanoACQUITY UPLC System (Waters). In-gel digested peptides (2 µl) was desalted in Symmetry C18 trapping column, 180 µm×20 mm, 5 µm (Waters) for 5 min with 2% mobile phase B (0.1% formic acid in acetonitrile) at 8 µl/min. The desalted peptides were separated online in nanoACQUITY UPLC BEH130 C18 column, 1.7 µm, 75 µm×150 mm (Waters Milford, Mass.). The flow rate was 0.3 µl/min, and the column temperature was 35° C. Mobile phase A was composed of 0.1% formic acid while mobile phase B was 0.1% formic acid in acetonitrile, the 40 min gradient was from 2-40% B, in 25 min, 40-97% B in 5 min, 97% B 5 min and 10% B in 0.5 min, then 10% B for 5 min.

Mass spectrometry (MS) analysis was performed on LTQ-Orbitrap Velos Pro Mass Spectrometer (Thermo Fisher Scientific, San Jose, Calif.) using nanoelectrospray in positive ionization mode (CID) at 1.7 kV. The LTQ-Orbitrap Velos Pro was operated in a top-ten data dependent mode using survey scans at 60 000 resolution from 300 to 1800 m/z. Tandem MS scans were acquired with normalized collision energy of 35 V, normalized collision energy was set to 40% for HCD, Ion trap and orbitrap maximal injection times were set to 100 ms and 10 ms respectively. Raw data files were converted by Thermo Scientific MSFileReader 2.2, and analyzed by PEAKS studio 6.0 software (Bioinformatics Solutions Inc.). The peptide and fragment ion mass tolerances used were ±5 ppm and ±0.5 Da, respectively. The specified search parameters were carbamidomethylation of cysteine as fixed modification, oxidation of methionine as dynamic modification and tryptic digestion with 1 missed cleavages. De novo sequencing, database search and Spider program against Herceptin database with sequentially shortened antibody sequences from the N-terminal translational start were used based on the DNA coding sequences.

Size Exclusion Chromatography Analysis of Protein A Purified mAb to Measure Aggregation The aggregation of protein A purified mAb was determined using size exclusion chromatography (SEC) coupled to a UV-visible detector and a dynamic light scattering detector. The instrument setup and chromatography condition are described by Ho, S. C. L. et al. [Ho, S. C. L. et al. (2012) Journal of Biotechnology, 157, 130-139]. The hydrodynamic radius measured by the light scattering detector was used to calculate the molecular weight of the different components present under each peak. The relative mass amount of each component was quantified using the respective peak area detected by the UV detector.

Example 1: Expression Intensity of EMCV IRES Variants in CHO K1 Cells

25 EMCV IRES variants were generated by mutating ATG-10, ATG-11 or ATG-12 in the IRESwt (SEQ ID NO:1) individually or in combination to GTG, CTG, ACG, ATA or TTG or deleting ATG-11 and ATG-12 together with surrounding sequences for subtle control of gene expression (FIG. 1). The strengths of these IRES variants were determined using dual-luciferase bicistronic vectors (FIG. 3A) in transient transfections in CHO K1 cells. Rluc was arranged as the first cistron immediately downstream of the mCS promoter and Fluc was arranged as the second cistron downstream of each IRES variant. As expression of the first cistron (cap-dependent translation) is not affected by the downstream IRES-driven cistron (cap-independent translation) [Bouabe, H., et al. (2008) Nucleic Acids Research, 36; Hennecke, M. et al. (2001) Nucleic Acids Research, 29, 3327-3334], using Rluc as an internal standard to normalize the transfection efficiency allowed accurate determination of Fluc expression which reflects the strength of IRES variants. Transfection of each dual-luciferase vector was done in duplicates in 6-well plate cultures and repeated using independently prepared plasmids and cultures to ensure reproducibility of the results. The average relative strengths of each IRES variant that were determined by the two independent experiments are listed in FIG. 1. The small standard deviations indicate high accuracy of dual-luciferase system for determination of IRES strength.

All IRES mutants exhibited reduced strength in expressing a gene compared to the IRESwt (FIG. 1). The magnitude of reduction varied depending on the position and number of ATG mutated. Mutation of ATG-10 and ATG-12 to GTG slightly reduced the strength to 90.48% and 83.59%, respectively, while mutation of ATG-11 dramatically reduced the strength to 35.48%. This is consistent with previous reports that translation initiation of IRESwt occurs primarily at ATG-11, partially at ATG-12, and negligible at ATG-10 [Davies, M. V. and Kaufman, R. J. (1992) J. Virol., 66, 1924-1932; Kaminski, A. et al. (1994) EMBO Journal, 13, 1673-1681; Kaminski, A. et al. (1990) EMBO Journal, 9, 3753-3759]. Mutation of two ATGs had a combinatorial effect in reducing the strength of IRES. For instance, mutation of ATG-10 and ATG-12 alone to GTG reduced the strength to 90.48% and 83.59%, respectively, while mutation of both to GTG reduced the strength to 67.42%. Similarly, mutation of both ATG-10 and ATG-11 reduced the strength to 29.45% and mutation of both ATG-11 and ATG-12 reduced the strength to 0.98%. Interestingly, mutation of all three ATGs to GTG reduced the strength to 1.37%, demonstrating no further reduction compared to mutation of ATG-11 and ATG-12 together.

The type of bases which ATGs were mutated to affected the strength of IRES differently. Mutation of ATG-11 to CTG was least effective in reducing strength, giving strength of 45.18%, followed by ATA, GTG, TTG, and ACG in a descending order to 39.91%, 35.48%, 34.39%, and 33.25%. The rank that the type of base had on IRES strength changed when both ATG-11 and ATG-12 or all three ATGs were mutated, giving an order of CTG>ACG>ATA>GTG>TTG with strengths covering a range from 13.58% to 0.58%. Mutation of all three ATGs exhibited further reduced strength compared to mutation of both ATG-11 and ATG-12 in some cases, such as ACG and ATA, but not in other cases, such as CTG, GTG, and TTG. Deletion of ATG-12 or ATG-11 together with surrounding sequences was also effective in reducing IRES strength. The IRES variant with ATG-10 and ATG-11 maintained and IRES variant with only ATG-10 left had strengths of 86.42% and 24.35%, respectively. Further mutation of ATGs in these two IRES generated three new IRES variants with strengths reduced to 0.34%, 0.46, and 0.57%.

These twenty five IRES mutants were sorted according to their relative strengths to the IRESwt in descending order with IRESv1 referring to the strongest variant and IRESv24 referring to the weakest variant (FIG. 1). The whole set of IRES variants enabled controlling expression of Fluc over a 300-fold range with small intervals (FIG. 4). To determine whether the differential expression from IRES variants is due to changes in translation efficiency, the Rluc and Fluc mRNA levels from each dual-luciferase vector were analyzed by qRT-PCR. Changes in Fluc mRNA levels were presented as the ratios of mRNA level of Fluc to Rluc normalized to the IRESwt. Differences in normalized Fluc mRNA levels were insignificant at 95% confidence level, suggesting that IRES variants controlled expression of a gene at translational levels (data not shown).

Example 2: Evaluation of EMCV IRES Variants in Different Mammalian Cell Lines

Figure 5:
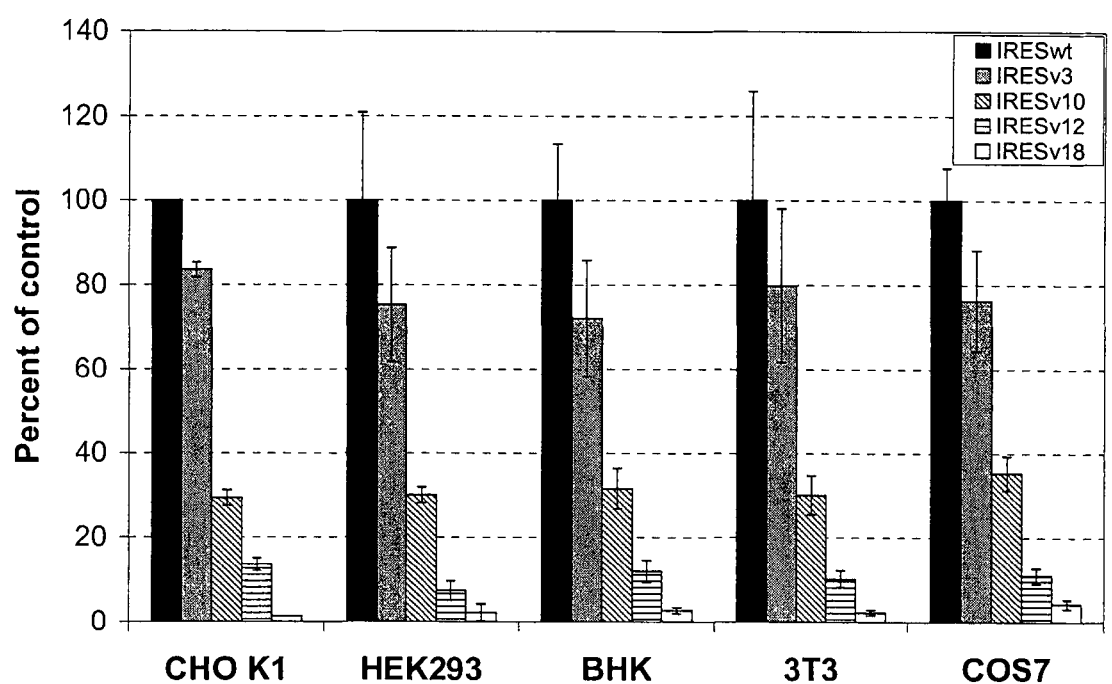
FIG. 5 shows the relative strength of IRES variants in different mammalian cell lines in transient transfections. The indicated strength of IRES variants in CHO K1 cells is the same as in FIG. 1. The strength of IRES variants in other cell lines was obtained by transfection of dual-luciferase vectors (FIG. 3A) containing, different IRES variants including V3, V10, V12, or V18 on the Fluc gene. At 48 h post-transfection, the luciferase activities of Rluc and Fluc gene were quantified by Dual-Glo Luciferase Assay Systems. Results represent the strength of each IRES variant calculated as the ratios of luciferase activities of Fluc to Rluc normalized to the control, the wild type EMCV IRES (IRESwt). Each point represents the average and standard deviation of eight measurements from two transfections.

To evaluate the application of IRES variants in different mammalian cell lines, the IRESwt and four representative IRES variants, IRESv3, IRESv10, IRESv12, and IRESv18 that exhibited significantly different strengths in CHO K1 cells were tested in a total of five different cell lines. The five cell lines represent a wide range of species and tissues: CHO K1 from Chinese hamster ovary, HEK293 from human embryonic kidney, BHK from baby hamster kidney, 3T3 from mouse embryo, and COST from African Green Monkey kidney. The first three cell lines have been used widely for production of recombinant proteins in industry and the last two have been used in fundamental biological studies. The four IRES variants exhibited similar relative strengths to the WT in expressing a gene in all different cell lines (FIG. 5). The IRESwt was the strongest in all cases, followed by IRESv3, IRESv10, IRESv12, and IRESv18.

Example 3: Application of EMCV IRES Variants for Enhancing the Selection Stringency The generated EMCV IRES variants, which can reduce the expression level of a gene up to below 1.00%, provide the opportunity to weaken the selection markers for maximizing the stringency of selection for high producing stable transfectants because one effective strategy to enrich high producing cells in a stably transfected pool is to reduce the expression of selection marker genes, as only clones with greater transcriptional activity or more copies of the integrated vector can survive the selection process when the selection marker is weakened [Ho, S. C. L. et al. (2012) Journal of Biotechnology, 157, 130-139].

To demonstrate application of IRES variants for the purpose of enhancing selection stringency, a series of anti-Her2 mAb was constructed expressed from tricistronic vectors with different strengths of IRES variants applied on the selection marker zeocin or DHFR (FIG. 3B). These vectors were then transfected into CHO K1 or DG44 cells to generate stable transfection pools. When the IRESwt was applied on zeocin, the titer of stably transfected CHO K1 pools at the end of shake flask batch culture was only 17.25 mg/L (FIG. 6A). Application of IRESv11 and IRESv13 with strengths reduced to 24.35% and 9.47% slightly increased the mAb titers to 28.83 and 24.65 mg/L, respectively. Using IRESv18 with further reduced strength to 1.37% dramatically increased the titer by more than 4-fold compared to the IRESwt, reaching 71.85 mg/L. However, using IRESv20 with strength of 0.65% did not result in further increased titer but decreasing the titer to 11.8 mg/L. When the same set of IRES variants was applied on DHFR, a trend similar to zeocin was observed for the relationship between the strengths of IRES variants and mAb titers (FIG. 6B). The titer of stable pools generated using the IRESwt were only 1.95 mg/L under selection of HT removal. Amplification at MTX 50 nM and 250 nM continuously increased the titer to 2.91 and 13.45 mg/L. When IRESv11 and IRESv13 were applied, the titer of stably transfected pools quickly increased up to 132.5 and 193.5 mg/L at MTX 250 nM, respectively. Application of IRESv18 exhibited increase in titer compared to IRESwt under selection of HT removal but amplification for enhanced titers was not successful. Using IRESv20 did not result in increase of titers under any selection conditions.

Example 4: Application of EMCV IRES Variants for Controlling LC Over HC Expressions The application of EMCV IRES variants for controlling the expression level of multiple genes was further demonstrated by expressing a particular multi-subunit protein, IgG mAb. An IgG molecule is composed of two identical LC and two identical HC polypeptides linked by disulfide bonds. To study the impact of LC:HC ratios on mAb expression, a basic anti-HER2 mAb expressing tricistronic vector was constructed with both LC and HC under the control of IRESwt (FIG. 3C). It was expected that this design would express LC and HC at similar levels. HP was placed in front of DHFR to reduce its expression for enhancing stable expression levels [de Quinto, S. L. and Martinez-Salas, E. (1998) Gene, 217, 51-56]. Another six vectors were then constructed by replacing IRESwt with IRES variants of IRESv3, IRESv10, and IRESv18 for different LC:HC ratios. CHO DG44 cells were transfected with these vectors and then undergone selection and amplification with MTX to generate stable transfection pools. These pools were characterized in shake flask batch cultures for intracellular LC:HC polypeptide ratios, mAb yield, and mAb quality.

Figure 7:
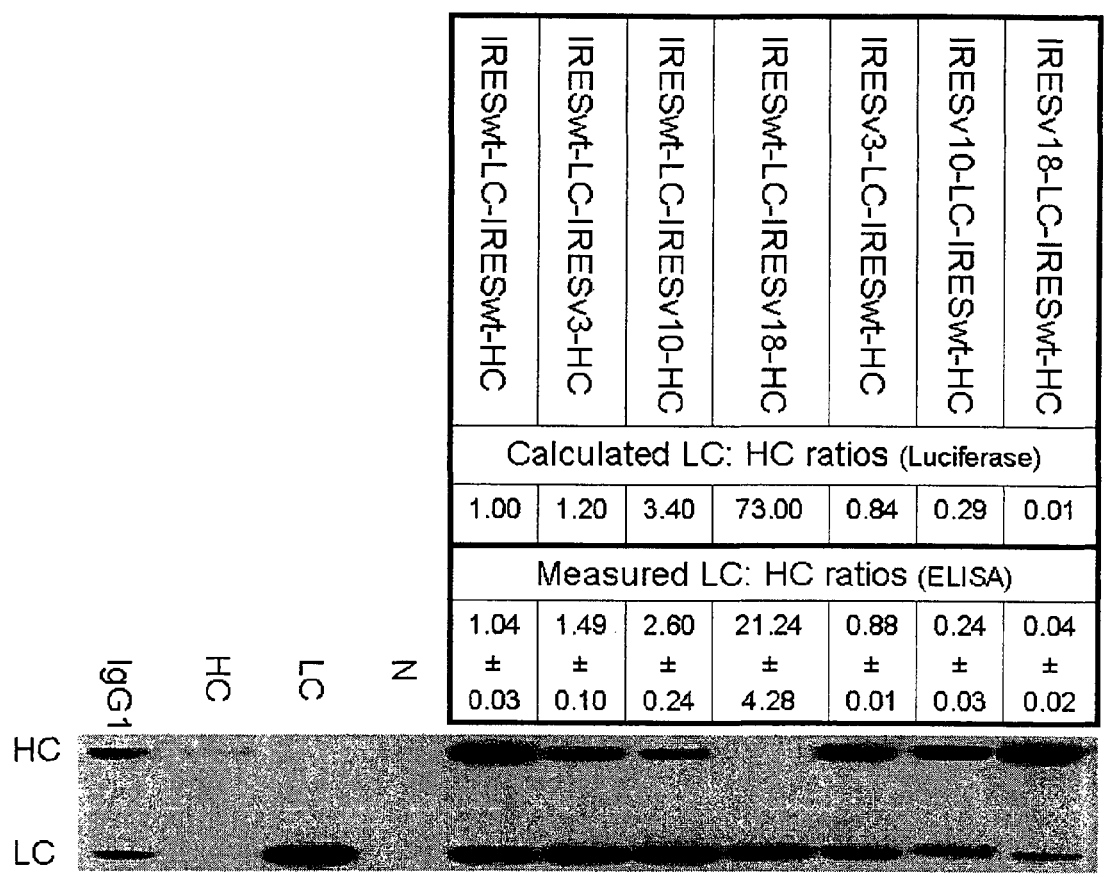
FIG. 7 shows a control of LC and HC expression using different IRES variants in stable transfections. CHO DG44 stable transfection pools were generated by transfection of tricistronic vectors with different IRES variants applied on the LC and HC cDNA (FIG. 3C). The ATG 10th, 11th, and 12th in each IRES variant were either conserved or mutated as indicated in FIG. 1. Cell pellets of stable transfection pools were collected at exponential growth and lysed using RIPA buffer. The concentration of LC and HC polypeptides in the lysates was determined by using ELISA, with detection antibody targeting LC and Fc region, respectively. Ratios of intracellular abundance of LC over HC polypeptides listed in the table were determined as the measured LC concentration divided by the HC concentration. Each point represents the average and standard deviation of four measurements from two stable transfection pools. The calculated LC:HC ratios were obtained based on the strengths of IRES variants determined by dual-luciferase system. For instance, the LC:HC ratio was calculated as 100 divided by 83.59 to get 1.20 when IRESwt and IRESv3 were applied on the LC and HC gene, respectively. The intracellular abundance of LC and HC polypeptides were also analyzed using western blot under reducing conditions. Cell lysates containing equal amounts of proteins were loaded into each lane. A commercial human affinity purified myeloma Ig1 (Sigma-Aldrich) and supernatants from cells transfected with either a vector expressing only HC or a vector expressing only LC were used as positive control, and supernatant from non-transfected cells as negative control (N). All blots shown are only from one set of stable transfection pools as similar result was obtained from the second set of stable transfection pools.

Intracellular LC:HC polypeptide ratios in stable pools generated using different vectors were determined using ELISA (FIG. 7). The basic vector with IRESwt applied on both LC and HC presented a LC:HC ratio of 1.04. Application of weaker IRESv3, IRESv10, and IRESv18 on HC increased the LC:HC ratios to 1.49, 2.60, and 21.24, while on LC decreased the ratios to 0.88, 0.24, and 0.04. The ELISA measured LC:HC ratios were similar to the LC:HC ratios calculated based on the strengths of IRES variants determined by the dual-luciferase system. Some differences in the values could be due to differences in translation efficiency of luciferase and antibody genes. Western blotting analysis of the same intracellular lysates prepared for ELISA was performed to verify the LC:HC ratios determined by ELISA. Cellular lysates containing equal amount of proteins were reduced and loaded into each lane of NuPAGE gel. The band intensities for LC and HC under the control of IRESwt were not significantly changed across different vectors, indicating that the expression of LC and HC can be independently altered by IRES variants without interference between each other. The band intensities corresponding to LC and HC polypeptide abundance were steadily decreased by weak IRES variants, suggesting that the altered LC:HC ratios were achieved by reducing either LC or HC expressions. The band corresponding to HC under the control of V18 was not visible due to low expression.

Figure 8:
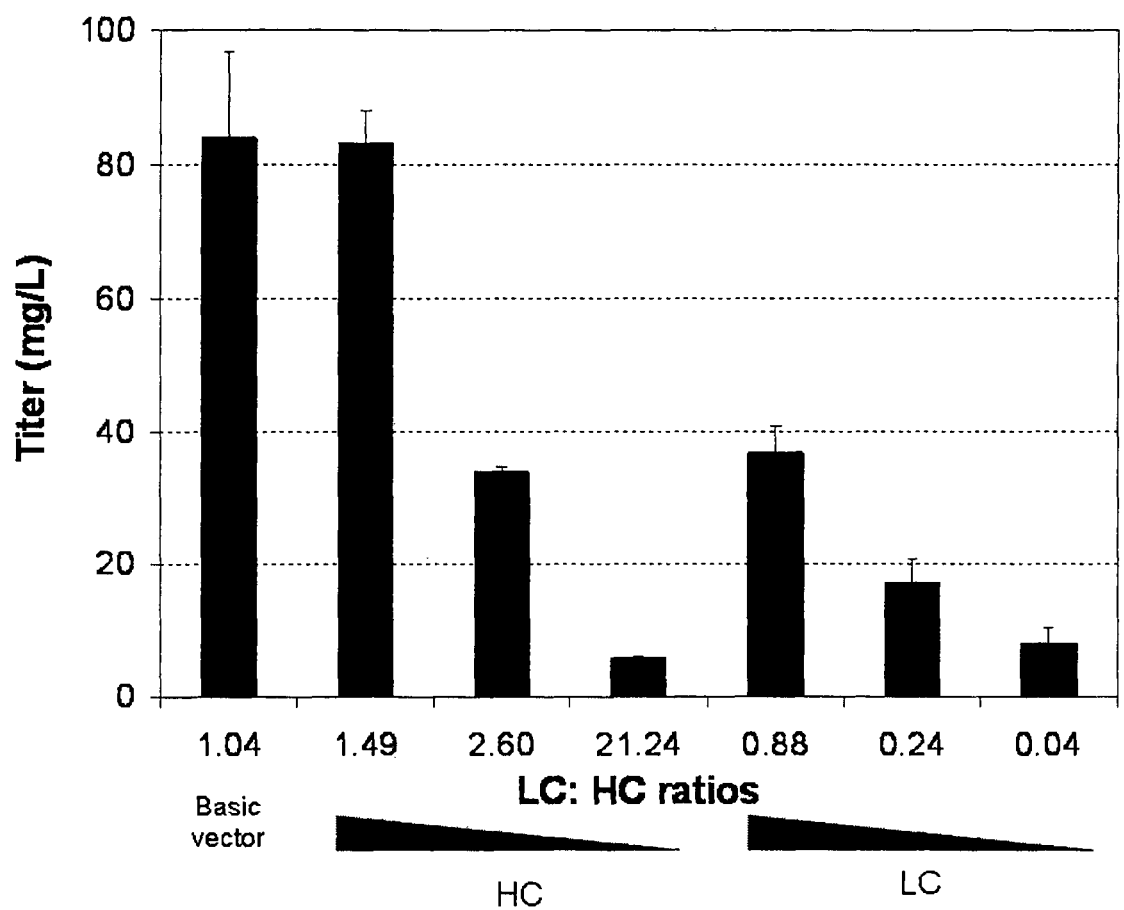
FIG. 8 shows the effect of LC and HC expression levels on mAb productivity in stable transfection pools. CHO DG44 stable transfection pools having different LC:HC ratios were cultured in shake flask batch cultures. Titers of monoclonal antibody at the end of culture were determined using a nephelometric method. Each point represents the average and standard deviation of measurements from two stable transfection pools.

The impact of LC:HC ratio on mAb yield was analyzed by plotting the end-point titer in shake flask batch culture against the LC:HC ratios as determined by ELISA (FIG. 8). The basic vector which controlled LC:HC ratio at 1.02 gave the highest titer of 84.1 mg/L. Slightly increasing the ratio to 1.49 by decreasing HC expression did not change titer significantly, yielding a titer of 83.3 mg/L. Further increasing the LC:HC ratios to 2.60 and 21.24 by decreasing the HC expression dramatically reduced the mAb titers to 34.0 and 5.9 mg/L, respectively. In contrast, a slight decrease of LC:HC ratio to 0.88 by decreasing the LC expression resulted in a sharp decline of mAb titer to 36.8 mg/L. The titer continuously dropped to 17.1 and 8.1 mg/L when LC:HC ratios decreased to 0.24 and 0.04 by further reducing LC expressions.

Figure 9:
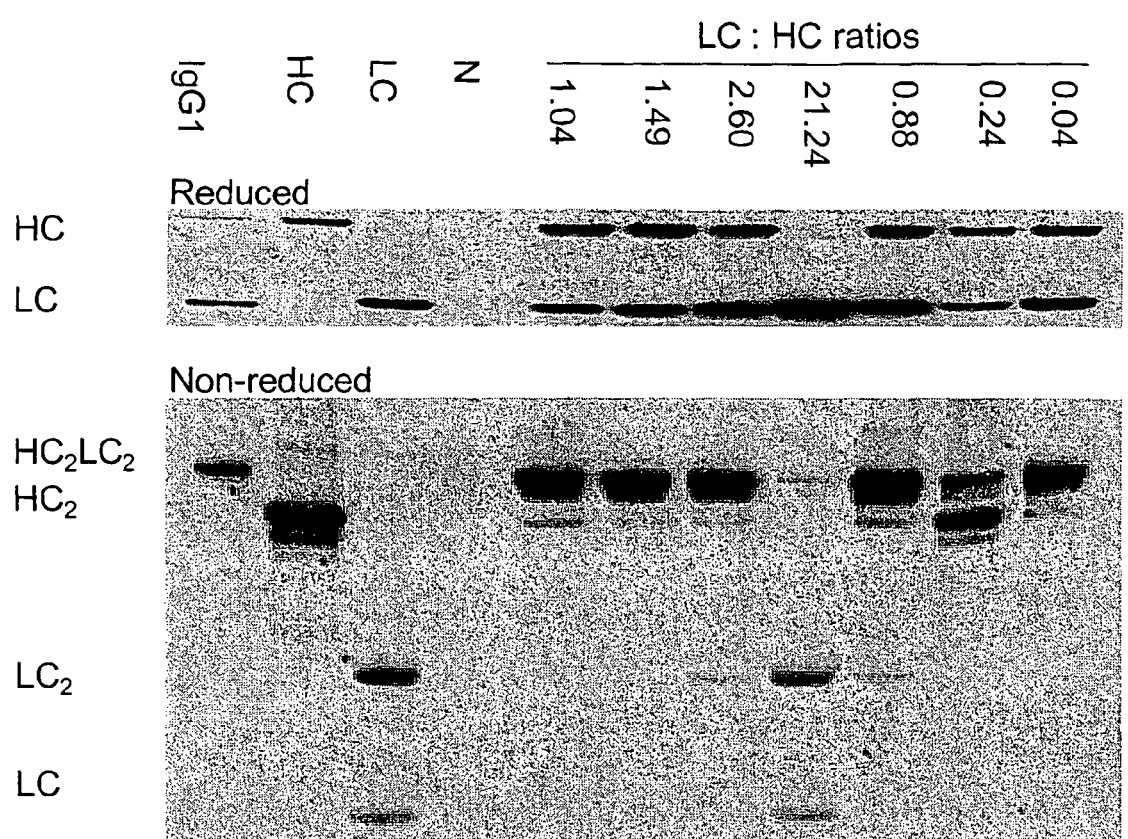
FIG. 9 shows a western blot analysis of supernatant from stable transfection pools expressing different LC:HC ratios. CHO DG44 stable transfection pools having different LC:HC ratios were cultured in shake flask batch cultures. Crude supernatant collected at the end of culture was analyzed under both reducing and non-reducing conditions by western blot. Positive and negative controls are the same as described in FIG. 8. Blots from only one set of stable transfection pools are shown as same product pattern were observed from the second set of stable transfection pools.

The qualities of mAb product produced in stable pools at different LC:HC ratios were first characterized by western blotting analysis of culture supernatant under non-reducing reducing conditions (FIG. 9). Supernatant containing same amount of antibody determined by ELISA was loaded into each lane of NuPAGE gel. Less amount of antibody was loaded for sample at the LC:HC ratio of 21.24 to avoid overexposure of LC fragments. Product from the basic vector with the LC:HC ratio of 1.04 contained complete IgG monomers HC2LC2 and a slight band corresponding to HC2 dimers, suggesting inefficient usage of HC polypeptides in mAb synthesis. Increasing LC:HC ratios to 1.49 and 2.60 by reducing HC expression resulted in secretion of less HC2 dimers. Further increasing the ratio to 21.24 eliminated secretion of HC2 dimers but resulted in secretion of LC2 dimers and LC monomers beside the complete IgG monomers, suggesting inefficient usage of LC polypeptides in mAb synthesis. In contrast, decreases in LC:HC ratios to 0.88, 0.24, and 0.04 resulted in secretion of HC2 dimmers besides the complete IgG monomer, suggesting inefficient usage of HC polypeptides in mAb synthesis. Western blotting analysis of reduced products in supernatant was next performed. LC and HC polypeptides expressed from all different IRES variants had similar sizes compared to standard LC and HC polypeptides. HC band at the LC:HC ratio of 21.24 was not observed due to lower amount of sample loading.

To obtain a more accurate protein characterization than Western blotting, protein A purified products in stable pools at different LC:HC ratios were separated on SDS-PAGE under reducing conditions. The excised bands corresponding to LC and HC polypeptides were digested by trypsin and then analyzed on LC-MS/MS for the signal peptide cleavage sites (FIG. 10). The N-terminal tryptic peptide sequences of both LC and HC were confirmed by MS/MS via de novo and database matching using PEAKS program. Trypsin cuts R and K. Detection of peptide DIQMTQSPSSLSASVGDR (SEQ ID NO:27) and EVQLVESGGGLVQPGGSLR (SEQ ID NO:28) indicated that signal peptides of LC and HC were both cleaved at correct sites, respectively. No miscleavaged signal peptide was observed on LC and HC in stable pools at LC:HC ratios of 1.04, 1.49, 2.60, 0.88, and 0.04, confirming integrity of product expressed from IRES variants. LC-MS/MS analyses of products in stable pools at LC:HC ratios of 21.24 and 0.04 were not performed because the amount of mAb produced were not enough.

Figure 11:
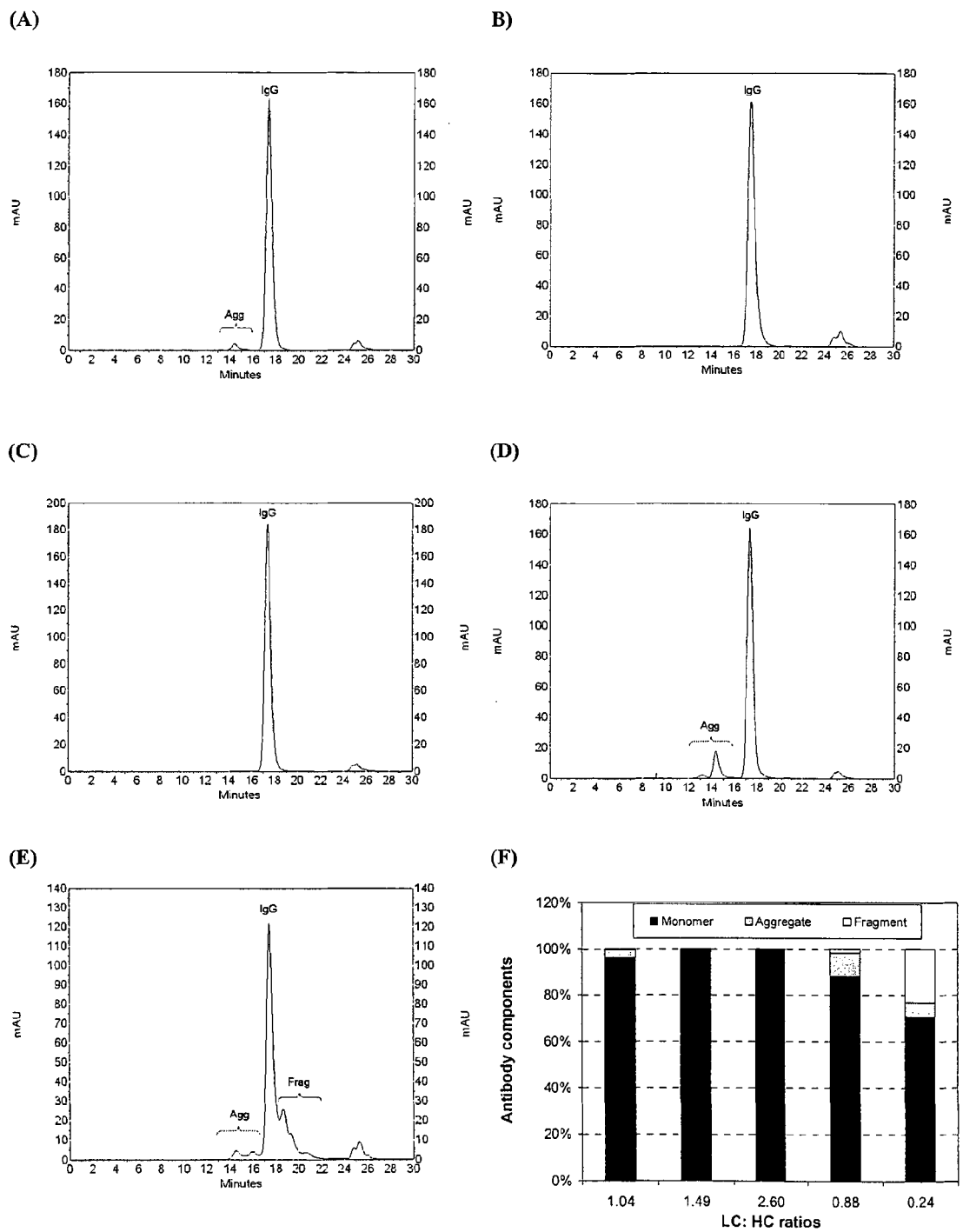
FIG. 11 shows representative SEC chromatograms and distribution of complete IgG monomer, aggregate, and incomplete IgG fragments produced in stable transfection pools at different LC:HC ratios. Components of protein A purified supernatant collected at the end of culture were separated by SEC followed by the identification and quantification of species by light scattering and UV detection, respectively. Analysis was done for duplicate stable transfection pools. Only one typical chromatogram of the first pools analyzed from UV detector for pools of (A) LC:HC=1.02, (B) LC:HC=1.40, (C) LC:HC=2.60, (D) LC:HC=0.88, and (E) LC:HC=0.24 is shown as results are consistent between two pools. Agg: Aggregates; IgG: complete IgG monomer; Frag: Incomplete IgG fragments. (F) Quantitative comparison of complete IgG monomer, aggregates, and incomplete IgG fragments for different LC:HC ratios. Each bar in figure F represents the average and standard deviation of four measurements from two stable transfection pools.

Finally, the impact of LC:HC ratio on mAb aggregation was analyzed by using SEC coupled to a dynamic light scattering detector and UV detector. Supernatant collected at the end of culture was purified by protein A before SEC analysis. One set of representative UV chromatograms for LC:HC ratios of 1.04, 1.49, 2.60, 0.88, and 0.24 is shown in FIG. 11A to 12E. SEC analysis of products in stable pools at LC:HC ratios of 21.24 and 0.04 were not performed because the amount of mAb produced were not enough. The molecular weight of each peak was calculated based on hydrodynamic radius determined by the light scattering (data not shown). Peaks with average molecular weight greater and lower than the complete IgG monomers were grouped as aggregates and incomplete mAb fragments, respectively. Relative mass amounts of aggregate, complete IgG monomer, and incomplete mAb fragment were quantified using the respective peak area under the UV chromatograms. Analysis was done for duplicate stable transfection pools at each LC:HC ratio. Average distributions of components at different LC:HC ratios are shown in FIG. 11F. Product at LC:HC ratio of 1.02 contained 96.2% IgG monomers, 3.6% aggregates, and 0.2% fragments. Increasing the ratio to 1.49 and 2.60 resulted in increase of IgG monomers to more than 99.3% and decrease of both aggregates and fragments to less than 0.5%. In contrast, decreasing the LC:HC ratio to 0.88 resulted in decrease of IgG monomers to 88.1% and increase of aggregates to 10.1% and fragments to 1.8%, respectively. Further decreasing the ratio to 0.24 did not lead to the formation of more aggregates but resulting in a sharp increase of fragments to 23.3% and thus decreasing IgG monomers to only 70.6%.

The invention has been described broadly and generically herein. Each of the narrower species and subgeneric groupings falling within the generic disclosure also form part of the invention. This includes the generic description of the invention with a proviso or negative limitation removing any subject-matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," "containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

The invention claimed is:

1. Nucleic acid molecule comprising a first internal ribosome entry site (IRES) sequence, wherein the first IRES sequence is a mutant IRES sequence and comprises a nucleotide sequence selected from the group consisting of any one of the nucleotides sequences set forth in SEQ ID Nos. 9-12, 19 and 21.

2. Nucleic acid molecule according to claim 1, further comprising a nucleotide sequence encoding a gene of interest A, wherein the mutant IRES sequence and the nucleotide sequence encoding a gene of interest A are operably linked.

3. Nucleic acid molecule according to claim 2, wherein the nucleic acid molecule further comprises a nucleotide sequence encoding a gene of interest B.

4. Nucleic acid molecule according to claim 3, wherein the gene of interest B is operably linked to a second IRES sequence.

5. Nucleic acid molecule according to claim 3, wherein the gene of interest B comprises a nucleic acid sequence encoding a light chain of an antibody.

6. Nucleic acid molecule according to claim 4, wherein the nucleic acid molecule comprises a gene of interest C operably linked to a third IRES.

7. Nucleic acid molecule according to claim 6, wherein the gene of interest C comprises a nucleic acid sequence encoding a heavy chain of an antibody.

8. Nucleic acid molecule according to claim 6, wherein the nucleic acid molecule comprises one or more further genes of interest, each operably linked to an IRES sequence.

9. Nucleic acid molecule according to claim 8, wherein the second and/or third and/or any further IRES sequence independently is a wild type IRES or a mutant IRES sequence that differs from a wild type IRES sequence at one or more ATG translation initiation site(s).

10. Nucleic acid molecule according to claim 9, wherein the second and/or third and/or any further IRES sequence independently comprises of a nucleotide sequence selected from the group consisting of any one of the nucleotides sequences set forth in SEQ ID Nos. 9-12, 19 and 21.

11. Nucleic acid molecule according to claim 1, wherein the mutant IRES sequence comprises a short DNA sequence which contains an additional out-of-frame ATG and has the capacity to form a hairpin structure.

12. Nucleic acid molecule according to claim 1, wherein said nucleic acid molecule is a DNA molecule.

13. Nucleic acid molecule according to claim 12, wherein said nucleic acid molecule comprises gene of interest A and the mutant IRES sequence and further comprises genes of interest B and C and second and third IRES sequences wherein the order of the elements on the coding strand is:
   5'-second IRES-gene of interest B-mutant IRES-gene of interest A-third IRES-gene of interest C-3'.

14. Nucleic acid molecule according to claim 1, wherein the gene of interest A encodes a selection marker.

15. Nucleic acid molecule according to claim 1, wherein said nucleic acid molecule is comprised in a vector.

16. Nucleic acid molecule according to claim 2, further comprising a promoter operably linked to the gene of interest A and the mutant IRES sequence.

17. A method of identifying cells that provide for enhanced gene expression comprising the steps of:
   (i) constructing a cell-based expression system comprising a promoter, a gene encoding for a selection marker, one or more genes of interest different from the selection marker gene, and a mutant IRES sequence that comprises a nucleotide sequence selected from the group consisting of any one of the nucleotides sequences set forth in SEQ ID Nos. 9-12, 19 and 21, wherein the mutant IRES sequence is operably linked to the gene encoding for a selection marker but not the one or more genes of interest;
   (ii) incubating the expression system under conditions that allow expression of the selection marker and the one or more genes of interest; and
   (iii) selecting for the selection marker, thus identifying the cells that provide for enhanced gene expression.

18. The method according to claim 17, wherein the order of the elements on the coding strand is
   :5'-promoter-gene of interest-mutant IRES-selection marker-3'.

19. The method according to claim 17, wherein the one or more genes of interest are operably linked to an IRES sequence, wherein said IRES sequence is a wildtype IRES sequence or a mutant IRES sequence that differs from a wild type IRES sequence at one or more ATG translation initiation site(s).

* * * * *

SEQUENCE LISTING

```
<160> NUMBER OF SEQ ID NOS: 28

<210> SEQ ID NO 1
<211> LENGTH: 590
<212> TYPE: DNA
<213> ORGANISM: Encephalomyocarditis virus

<400> SEQUENCE: 1 ccctctccc tcccccccc ctaacgttac tggccgaagc cgcttggaat aaggccggtg      60
tgcgtttgtc tatatgttat tttccaccat attgccgtct tttggcaatg tgagggcccg    120
gaaacctggc cctgtcttct tgacgagcat tcctaggggg ctttcccctc tcgccaaagg    180
aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggta    480
cacatgcttt acatgtgttt agtcgaggtt aaaaaaacgt ctaggccccc cgaaccacgg    540
ggacgtggtt ttcctttgaa aaacacgatg ataatatggc cacaaccatg               590

<210> SEQ ID NO 2
<211> LENGTH: 590
<212> TYPE: DNA
```

<213> ORGANISM: Artificial Sequence
<220> FEATURE:
<223> OTHER INFORMATION: mutatated IRES

<400> SEQUENCE: 2

```
cccctctccc tcccccccc ctaacgttac tggccgaagc cgcttggaat aaggccggtg      60
tgcgtttgtc tatatgttat tttccaccat attgccgtct tttggcaatg tgagggcccg    120
gaaacctggc cctgtcttct tgacgagcat tcctagggt cttccctc tcgccaaagg      180
aatgcaaggt ctgttgaatg tcgtgaagga agcagttcct ctggaagctt cttgaagaca    240
aacaacgtct gtagcgaccc tttgcaggca gcggaacccc ccacctgcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggta    480
cacatgcttt acatgtgttt agtcgaggtt aaaaaaacgt ctaggccccc cgaaccacgg    540
ggacgtggtt ttcctttgaa aaacacggtg ataatatggc cacaaccatg              590
```

<210> SEQ ID NO 3
<211> LENGTH: 590
<212> TYPE: DNA
<213> ORGANISM: Artificial Sequence
<220> FEATURE:
<223> OTHER INFORMATION: mutatated IRES

<400> SEQUENCE: 3

```
cccctctccc tcccccccc ctaacgttac tggccgaagc cgcttggaat aaggccggtg      60
tgcgtttgtc tatatgttat tttccaccat attgccgtct tttggcaatg tgagggcccg    120
gaaacctggc cctgtcttct tgacgagcat tcctagggt cttccctc tcgccaaagg      180
aatgcaaggt ctgttgaatg tcgtgaagga agcagttcct ctggaagctt cttgaagaca    240
aacaacgtct gtagcgaccc tttgcaggca gcggaacccc ccacctgcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggta    480
cacatgcttt acatgtgttt agtcgaggtt aaaaaaacgt ctaggccccc cgaaccacgg    540
ggacgtggtt ttcctttgaa aaacacgatg ataatatggc cacaaccgtg              590
```

<210> SEQ ID NO 4
<211> LENGTH: 590
<212> TYPE: DNA
<213> ORGANISM: Artificial Sequence
<220> FEATURE:
<223> OTHER INFORMATION: mutatated IRES

<400> SEQUENCE: 4

```
cccctctccc tcccccccc ctaacgttac tggccgaagc cgcttggaat aaggccggtg      60
tgcgtttgtc tatatgttat tttccaccat attgccgtct tttggcaatg tgagggcccg    120
gaaacctggc cctgtcttct tgacgagcat tcctagggt cttccctc tcgccaaagg      180
aatgcaaggt ctgttgaatg tcgtgaagga agcagttcct ctggaagctt cttgaagaca    240
aacaacgtct gtagcgaccc tttgcaggca gcggaacccc ccacctgcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
```

```
ggggctgaag gatgcccaga aggtacccca ttgtatggga tctgatctgg ggcctcggta        480
cacatgcttt acatgtgttt agtcgaggtt aaaaaaacgt ctaggccccc cgaaccacgg        540
ggacgtggtt ttcctttgaa aaacacgatg ataatgtggc cacaaccatg                   590
```

<210> SEQ ID NO 5
<211> LENGTH: 590
<212> TYPE: DNA
<213> ORGANISM: Artificial Sequence
<220> FEATURE:
<223> OTHER INFORMATION: mutatated IRES

<400> SEQUENCE: 5

```
cccctctccc tcccccccc ctaacgttac tggccgaagc cgcttggaat aaggccggtg          60
tgcgtttgtc tatatgttat tttccaccat attgccgtct tttggcaatg tgagggcccg        120
gaaacctggc cctgtcttct tgacgagcat cctagggggt cttccccctc tcgccaaagg        180
aatgcaaggt ctgttgaatg tcgtgaagga agcagttcct ctggaagctt cttgaagaca        240
aacaacgtct gtagcgaccc tttgcaggca gcggaacccc ccacctggcg acaggtgcct        300
ctgcggccaa aagccacgtg tataagatac acctgcaaag gcggcacaac cccagtgcca        360
cgttgtgagt tggatagttg tggaaagagt caaatggctc tcctcaagcg tattcaacaa        420
ggggctgaag gatgcccaga aggtacccca ttgtatggga tctgatctgg ggcctcggta        480
cacatgcttt acatgtgttt agtcgaggtt aaaaaaacgt ctaggccccc cgaaccacgg        540
ggacgtggtt ttcctttgaa aaacacggtg ataatatggc cacaaccgtg                   590
```

<210> SEQ ID NO 6
<211> LENGTH: 590
<212> TYPE: DNA
<213> ORGANISM: Artificial Sequence
<220> FEATURE:
<223> OTHER INFORMATION: mutatated IRES

<400> SEQUENCE: 6

```
cccctctccc tcccccccc ctaacgttac tggccgaagc cgcttggaat aaggccggtg          60
tgcgtttgtc tatatgttat tttccaccat attgccgtct tttggcaatg tgagggcccg        120
gaaacctggc cctgtcttct tgacgagcat cctagggggt cttccccctc tcgccaaagg        180
aatgcaaggt ctgttgaatg tcgtgaagga agcagttcct ctggaagctt cttgaagaca        240
aacaacgtct gtagcgaccc tttgcaggca gcggaacccc ccacctggcg acaggtgcct        300
ctgcggccaa aagccacgtg tataagatac acctgcaaag gcggcacaac cccagtgcca        360
cgttgtgagt tggatagttg tggaaagagt caaatggctc tcctcaagcg tattcaacaa        420
ggggctgaag gatgcccaga aggtacccca ttgtatggga tctgatctgg ggcctcggta        480
cacatgcttt acatgtgttt agtcgaggtt aaaaaaacgt ctaggccccc cgaaccacgg        540
ggacgtggtt ttcctttgaa aaacacggtg ataatgtggc cacaaccatg                   590
```

<210> SEQ ID NO 7
<211> LENGTH: 590
<212> TYPE: DNA
<213> ORGANISM: Artificial Sequence
<220> FEATURE:
<223> OTHER INFORMATION: mutatated IRES

<400> SEQUENCE: 7

```
cccctctccc tcccccccc ctaacgttac tggccgaagc cgcttggaat aaggccggtg          60
```

| | | |
|---|---|---|
| tgcgtttgtc tatatgttat tttccaccat attgccgtct tttggcaatg tgagggcccg | 120 | |
| gaaacctggc cctgtcttct tgacgagcat tcctagggt cttccctc tcgccaaagg | 180 | |
| aatgcaaggt ctgttgaatg tcgtgaagga agcagttcct ctggaagctt cttgaagaca | 240 | |
| aacaacgtct gtagcgaccc tttgcaggca gcggaacccc ccacctggcg acaggtgcct | 300 | |
| ctgcggccaa aagccacgtg tataagatac acctgcaaag gcggcacaac cccagtgcca | 360 | |
| cgttgtgagt tggatagttg tggaaagagt caaatggctc tcctcaagcg tattcaacaa | 420 | |
| ggggctgaag gatgcccaga aggtacccca ttgtatggga tctgatctgg ggcctcggta | 480 | |
| cacatgcttt acatgtgttt agtcgaggtt aaaaaaacgt ctaggccccc cgaaccacgg | 540 | |
| ggacgtggtt ttcctttgaa aaacacgatg ataatgtggc cacaaccgtg | 590 | |

<210> SEQ ID NO 8
<211> LENGTH: 590
<212> TYPE: DNA
<213> ORGANISM: Artificial Sequence
<220> FEATURE:
<223> OTHER INFORMATION: mutatated IRES

<400> SEQUENCE: 8

| | | |
|---|---|---|
| cccctctccc tccccccccc ctaacgttac tggccgaagc cgcttggaat aaggccggtg | 60 | |
| tgcgtttgtc tatatgttat tttccaccat attgccgtct tttggcaatg tgagggcccg | 120 | |
| gaaacctggc cctgtcttct tgacgagcat tcctagggt cttccctc tcgccaaagg | 180 | |
| aatgcaaggt ctgttgaatg tcgtgaagga agcagttcct ctggaagctt cttgaagaca | 240 | |
| aacaacgtct gtagcgaccc tttgcaggca gcggaacccc ccacctggcg acaggtgcct | 300 | |
| ctgcggccaa aagccacgtg tataagatac acctgcaaag gcggcacaac cccagtgcca | 360 | |
| cgttgtgagt tggatagttg tggaaagagt caaatggctc tcctcaagcg tattcaacaa | 420 | |
| ggggctgaag gatgcccaga aggtacccca ttgtatggga tctgatctgg ggcctcggta | 480 | |
| cacatgcttt acatgtgttt agtcgaggtt aaaaaaacgt ctaggccccc cgaaccacgg | 540 | |
| ggacgtggtt ttcctttgaa aaacacggtg ataatgtggc cacaaccgtg | 590 | |

<210> SEQ ID NO 9
<211> LENGTH: 590
<212> TYPE: DNA
<213> ORGANISM: Artificial Sequence
<220> FEATURE:
<223> OTHER INFORMATION: mutatated IRES

<400> SEQUENCE: 9

| | | |
|---|---|---|
| cccctctccc tccccccccc ctaacgttac tggccgaagc cgcttggaat aaggccggtg | 60 | |
| tgcgtttgtc tatatgttat tttccaccat attgccgtct tttggcaatg tgagggcccg | 120 | |
| gaaacctggc cctgtcttct tgacgagcat tcctagggt cttccctc tcgccaaagg | 180 | |
| aatgcaaggt ctgttgaatg tcgtgaagga agcagttcct ctggaagctt cttgaagaca | 240 | |
| aacaacgtct gtagcgaccc tttgcaggca gcggaacccc ccacctggcg acaggtgcct | 300 | |
| ctgcggccaa aagccacgtg tataagatac acctgcaaag gcggcacaac cccagtgcca | 360 | |
| cgttgtgagt tggatagttg tggaaagagt caaatggctc tcctcaagcg tattcaacaa | 420 | |
| ggggctgaag gatgcccaga aggtacccca ttgtatggga tctgatctgg ggcctcggta | 480 | |
| cacatgcttt acatgtgttt agtcgaggtt aaaaaaacgt ctaggccccc cgaaccacgg | 540 | |
| ggacgtggtt ttcctttgaa aaacacgatg ataatctggc cacaaccatg | 590 | |

```
<210> SEQ ID NO 10
<211> LENGTH: 590
<212> TYPE: DNA
<213> ORGANISM: Artificial Sequence
<220> FEATURE:
<223> OTHER INFORMATION: mutatated IRES

<400> SEQUENCE: 10
cccctctccc tcccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat tcctaggggt cttccctc tcgccaaagg      180 aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct     300
ctgcggccaa agccacgtg tataagatac acctgcaaag gcggcacaac cccagtgcca     360
cgttgtgagt tggatagttg tggaaagagt caaatggctc tcctcaagcg tattcaacaa     420
ggggctgaag gatgcccaga aggtacccca ttgtatggga tctgatctgg ggcctcggta     480
cacatgcttt acatgtgttt agtcgaggtt aaaaaaacgt ctaggccccc cgaaccacgg     540
ggacgtggtt ttcctttgaa aaacacgatg ataatatagc cacaaccatg              590

<210> SEQ ID NO 11
<211> LENGTH: 590
<212> TYPE: DNA
<213> ORGANISM: Artificial Sequence
<220> FEATURE:
<223> OTHER INFORMATION: mutatated IRES

<400> SEQUENCE: 11
cccctctccc tcccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat tcctaggggt cttccctc tcgccaaagg      180 aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct     300
ctgcggccaa agccacgtg tataagatac acctgcaaag gcggcacaac cccagtgcca     360
cgttgtgagt tggatagttg tggaaagagt caaatggctc tcctcaagcg tattcaacaa     420
ggggctgaag gatgcccaga aggtacccca ttgtatggga tctgatctgg ggcctcggta     480
cacatgcttt acatgtgttt agtcgaggtt aaaaaaacgt ctaggccccc cgaaccacgg     540
ggacgtggtt ttcctttgaa aaacacgatg ataatttggc cacaaccatg              590

<210> SEQ ID NO 12
<211> LENGTH: 590
<212> TYPE: DNA
<213> ORGANISM: Artificial Sequence
<220> FEATURE:
<223> OTHER INFORMATION: mutatated IRES

<400> SEQUENCE: 12
cccctctccc tcccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat tcctaggggt cttccctc tcgccaaagg      180 aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct     300
```

```
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggta    480
cacatgcttt acatgtgttt agtcgaggtt aaaaaaacgt ctaggccccc cgaaccacgg    540
ggacgtggtt ttcctttgaa aaacacgatg ataatacggc cacaaccatg               590
```

<210> SEQ ID NO 13
<211> LENGTH: 590
<212> TYPE: DNA
<213> ORGANISM: Artificial Sequence
<220> FEATURE:
<223> OTHER INFORMATION: mutatated IRES

<400> SEQUENCE: 13

```
cccctctccc tcccccccc ctaacgttac tggccgaagc cgcttggaat aaggccggtg     60
tgcgtttgtc tatatgttat tttccaccat attgccgtct tttggcaatg tgagggcccg   120
gaaacctggc cctgtcttct tgacgagcat cctagggggt ctttcccctc tcgccaaagg   180
aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtacccca ttgtatggga tctgatctgg ggcctcggta   480
cacatgcttt acatgtgttt agtcgaggtt aaaaaaacgt ctaggccccc cgaaccacgg   540
ggacgtggtt ttcctttgaa aaacacgatg ataatctggc cacaaccctg               590
```

<210> SEQ ID NO 14
<211> LENGTH: 590
<212> TYPE: DNA
<213> ORGANISM: Artificial Sequence
<220> FEATURE:
<223> OTHER INFORMATION: mutatated IRES

<400> SEQUENCE: 14

```
cccctctccc tcccccccc ctaacgttac tggccgaagc cgcttggaat aaggccggtg     60
tgcgtttgtc tatatgttat tttccaccat attgccgtct tttggcaatg tgagggcccg   120
gaaacctggc cctgtcttct tgacgagcat cctaggggt ctttcccctc tcgccaaagg    180
aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtacccca ttgtatggga tctgatctgg ggcctcggta   480
cacatgcttt acatgtgttt agtcgaggtt aaaaaaacgt ctaggccccc cgaaccacgg   540
ggacgtggtt ttcctttgaa aaacacgctg ataatctggc cacaaccctg               590
```

<210> SEQ ID NO 15
<211> LENGTH: 590
<212> TYPE: DNA
<213> ORGANISM: Artificial Sequence
<220> FEATURE:
<223> OTHER INFORMATION: mutatated IRES

<400> SEQUENCE: 15

```
cccctctccc tcccccccccc ctaacgttac tggccgaagc cgcttggaat aaggccggtg    60
tgcgtttgtc tatatgttat tttccaccat attgccgtct tttggcaatg tgagggcccg   120
gaaacctggc cctgtcttct tgacgagcat tcctaggggt cttttcccctc tcgccaaagg   180 aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtacccca ttgtatggga tctgatctgg ggcctcggta   480
cacatgcttt acatgtgttt agtcgaggtt aaaaaaacgt ctaggccccc cgaaccacgg   540
ggacgtggtt ttcctttgaa aaacacgatg ataatacggc cacaaccacg              590
```

<210> SEQ ID NO 16
<211> LENGTH: 590
<212> TYPE: DNA
<213> ORGANISM: Artificial Sequence
<220> FEATURE:
<223> OTHER INFORMATION: mutatated IRES

<400> SEQUENCE: 16

```
cccctctccc tcccccccccc ctaacgttac tggccgaagc cgcttggaat aaggccggtg    60
tgcgtttgtc tatatgttat tttccaccat attgccgtct tttggcaatg tgagggcccg   120
gaaacctggc cctgtcttct tgacgagcat tcctaggggt cttttcccctc tcgccaaagg   180 aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtacccca ttgtatggga tctgatctgg ggcctcggta   480
cacatgcttt acatgtgttt agtcgaggtt aaaaaaacgt ctaggccccc cgaaccacgg   540
ggacgtggtt ttcctttgaa aaacacgacg ataatacggc cacaaccacg              590
```

<210> SEQ ID NO 17
<211> LENGTH: 590
<212> TYPE: DNA
<213> ORGANISM: Artificial Sequence
<220> FEATURE:
<223> OTHER INFORMATION: mutatated IRES

<400> SEQUENCE: 17

```
cccctctccc tcccccccccc ctaacgttac tggccgaagc cgcttggaat aaggccggtg    60
tgcgtttgtc tatatgttat tttccaccat attgccgtct tttggcaatg tgagggcccg   120
gaaacctggc cctgtcttct tgacgagcat tcctaggggt cttttcccctc tcgccaaagg   180 aatgcaaggt ctgttgaatg tcgtgaagga agcagttcct ctggaagctt cttgaagaca   240
aacaacgtct gtagcgaccc tttgcaggca gcggaacccc ccacctggcg acaggtgcct   300
ctgcggccaa aagccacgtg tataagatac acctgcaaag gcggcacaac cccagtgcca   360
cgttgtgagt tggatagttg tggaaagagt caaatggctc tcctcaagcg tattcaacaa   420
ggggctgaag gatgcccaga aggtacccca ttgtatggga tctgatctgg ggcctcggta   480
cacatgcttt acatgtgttt agtcgaggtt aaaaaaacgt ctaggccccc cgaaccacgg   540
```
ggacgtggtt ttcctttgaa aaacacgatg ataatatagc cacaaccata        590

<210> SEQ ID NO 18
<211> LENGTH: 590
<212> TYPE: DNA
<213> ORGANISM: Artificial Sequence
<220> FEATURE:
<223> OTHER INFORMATION: mutatated IRES

<400> SEQUENCE: 18
cccctctccc tcccccccc ctaacgttac tggccgaagc cgcttggaat aaggccggtg        60
tgcgtttgtc tatatgttat tttccaccat attgccgtct tttggcaatg tgagggcccg      120
gaaacctggc cctgtcttct tgacgagcat tcctaggggt cttccccctc tcgccaaagg      180
aatgcaaggt ctgttgaatg tcgtgaagga agcagttcct ctggaagctt cttgaagaca      240
aacaacgtct gtagcgaccc tttgcaggca gcggaacccc ccacctggcg acaggtgcct      300
ctgcggccaa aagccacgtg tataagatac acctgcaaag gcggcacaac cccagtgcca      360
cgttgtgagt tggatagttg tggaaagagt caaatggctc tcctcaagcg tattcaacaa      420
ggggctgaag gatgcccaga aggtaccccca ttgtatggga tctgatctgg ggcctcggta      480
cacatgcttt acatgtgttt agtcgaggtt aaaaaaacgt ctaggccccc cgaaccacgg      540
ggacgtggtt ttcctttgaa aaacacgata ataatatagc cacaaccata       590

<210> SEQ ID NO 19
<211> LENGTH: 590
<212> TYPE: DNA
<213> ORGANISM: Artificial Sequence
<220> FEATURE:
<223> OTHER INFORMATION: mutatated IRES

<400> SEQUENCE: 19
cccctctccc tcccccccc ctaacgttac tggccgaagc cgcttggaat aaggccggtg        60
tgcgtttgtc tatatgttat tttccaccat attgccgtct tttggcaatg tgagggcccg      120
gaaacctggc cctgtcttct tgacgagcat tcctaggggt cttccccctc tcgccaaagg      180
aatgcaaggt ctgttgaatg tcgtgaagga agcagttcct ctggaagctt cttgaagaca      240
aacaacgtct gtagcgaccc tttgcaggca gcggaacccc ccacctggcg acaggtgcct      300
ctgcggccaa aagccacgtg tataagatac acctgcaaag gcggcacaac cccagtgcca      360
cgttgtgagt tggatagttg tggaaagagt caaatggctc tcctcaagcg tattcaacaa      420
ggggctgaag gatgcccaga aggtaccccca ttgtatggga tctgatctgg ggcctcggta      480
cacatgcttt acatgtgttt agtcgaggtt aaaaaaacgt ctaggccccc cgaaccacgg      540
ggacgtggtt ttcctttgaa aaacacgatg ataatttggc cacaaccttg       590

<210> SEQ ID NO 20
<211> LENGTH: 590
<212> TYPE: DNA
<213> ORGANISM: Artificial Sequence
<220> FEATURE:
<223> OTHER INFORMATION: mutatated IRES

<400> SEQUENCE: 20
cccctctccc tcccccccc ctaacgttac tggccgaagc cgcttggaat aaggccggtg        60
tgcgtttgtc tatatgttat tttccaccat attgccgtct tttggcaatg tgagggcccg      120
gaaacctggc cctgtcttct tgacgagcat tcctaggggt cttccccctc tcgccaaagg      180
aatgcaaggt ctgttgaatg tcgtgaagga agcagttcct ctggaagctt cttgaagaca      240

```
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggta    480
cacatgcttt acatgtgttt agtcgaggtt aaaaaaacgt ctaggccccc cgaaccacgg    540
ggacgtggtt ttcctttgaa aaacacgttg ataatttggc cacaaccttg              590

<210> SEQ ID NO 21
<211> LENGTH: 590
<212> TYPE: DNA
<213> ORGANISM: Artificial Sequence
<220> FEATURE:
<223> OTHER INFORMATION: mutatated IRES

<400> SEQUENCE: 21
cccctctccc tccccccccc ctaacgttac tggccgaagc cgcttggaat aaggccggtg     60
tgcgtttgtc tatatgttat tttccaccat attgccgtct tttggcaatg tgagggcccg    120
gaaacctggc cctgtcttct tgacgagcat tcctaggggt cttccctc tcgccaaagg     180 aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggta    480
cacatgcttt acatgtgttt agtcgaggtt aaaaaaacgt ctaggccccc cgaaccacgg    540
ggacgtggtt ttcctttgaa aaacacgatt ataatattgc cacaaccatt              590

<210> SEQ ID NO 22
<211> LENGTH: 578
<212> TYPE: DNA
<213> ORGANISM: Artificial Sequence
<220> FEATURE:
<223> OTHER INFORMATION: mutatated IRES

<400> SEQUENCE: 22
cccctctccc tccccccccc ctaacgttac tggccgaagc cgcttggaat aaggccggtg     60
tgcgtttgtc tatatgttat tttccaccat attgccgtct tttggcaatg tgagggcccg    120
gaaacctggc cctgtcttct tgacgagcat tcctaggggt cttccctc tcgccaaagg     180 aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggta    480
cacatgcttt acatgtgttt agtcgaggtt aaaaaaacgt ctaggccccc cgaaccacgg    540
ggacgtggtt ttcctttgaa aaacacgatg ataatatg                           578

<210> SEQ ID NO 23
<211> LENGTH: 570
<212> TYPE: DNA
<213> ORGANISM: Artificial Sequence
<220> FEATURE:
```

<223> OTHER INFORMATION: mutatated IRES

<400> SEQUENCE: 23

```
cccctctccc tccccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat tcctagggg ctttcccctc tcgccaaagg     180
aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct     300
ctgcggccaa aagccacgtg tataagatac acctgcaaag gcggcacaac cccagtgcca     360
cgttgtgagt tggatagttg tggaaagagt caaatggctc tcctcaagcg tattcaacaa     420
ggggctgaag gatgcccaga aggtacccca ttgtatggga tctgatctgg ggcctcggta     480
cacatgcttt acatgtgttt agtcgaggtt aaaaaaacgt ctaggccccc cgaaccacgg     540
ggacgtggtt ttcctttgaa aaacacgatg                                      570
```

<210> SEQ ID NO 24
<211> LENGTH: 578
<212> TYPE: DNA
<213> ORGANISM: Artificial Sequence
<220> FEATURE:
<223> OTHER INFORMATION: mutatated IRES

<400> SEQUENCE: 24

```
ccccctctccc tccccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat tcctagggg ctttcccctc tcgccaaagg     180
aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct     300
ctgcggccaa aagccacgtg tataagatac acctgcaaag gcggcacaac cccagtgcca     360
cgttgtgagt tggatagttg tggaaagagt caaatggctc tcctcaagcg tattcaacaa     420
ggggctgaag gatgcccaga aggtacccca ttgtatggga tctgatctgg ggcctcggta     480
cacatgcttt acatgtgttt agtcgaggtt aaaaaaacgt ctaggccccc cgaaccacgg     540
ggacgtggtt ttcctttgaa aaacacgatg ataatgtg                             578
```

<210> SEQ ID NO 25
<211> LENGTH: 578
<212> TYPE: DNA
<213> ORGANISM: Artificial Sequence
<220> FEATURE:
<223> OTHER INFORMATION: mutatated IRES

<400> SEQUENCE: 25

```
ccccctctccc tccccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat tcctagggg ctttcccctc tcgccaaagg     180
aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct     300
ctgcggccaa aagccacgtg tataagatac acctgcaaag gcggcacaac cccagtgcca     360
cgttgtgagt tggatagttg tggaaagagt caaatggctc tcctcaagcg tattcaacaa     420
ggggctgaag gatgcccaga aggtacccca ttgtatggga tctgatctgg ggcctcggta     480
```

```
cacatgcttt acatgtgttt agtcgaggtt aaaaaaacgt ctaggccccc cgaaccacgg    540
ggacgtggtt ttcctttgaa aaacacggtg ataatgtg                           578
```

<210> SEQ ID NO 26
<211> LENGTH: 570
<212> TYPE: DNA
<213> ORGANISM: Artificial Sequence
<220> FEATURE:
<223> OTHER INFORMATION: mutatated IRES

<400> SEQUENCE: 26

```
cccctctccc tccccccccc ctaacgttac tggccgaagc cgcttggaat aaggccggtg     60
tgcgtttgtc tatatgttat tttccaccat attgccgtct tttggcaatg tgagggcccg    120
gaaacctggc cctgtcttct tgacgagcat tcctaggggt cttcccctc tcgccaaagg    180 aatgcaaggt ctgttgaatg tcgtgaagga agcagttcct ctggaagctt cttgaagaca    240
aacaacgtct gtagcgaccc tttgcaggca gcggaacccc ccacctggcg acaggtgcct    300
ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtacccca ttgtatggga tctgatctgg ggcctcggta    480
cacatgcttt acatgtgttt agtcgaggtt aaaaaaacgt ctaggccccc cgaaccacgg    540
ggacgtggtt ttcctttgaa aaacacggtg                                    570
```

<210> SEQ ID NO 27
<211> LENGTH: 18
<212> TYPE: PRT
<213> ORGANISM: Artificial Sequence
<220> FEATURE:
<223> OTHER INFORMATION: mAb fragment

<400> SEQUENCE: 27

```
Asp Ile Gln Met Thr Gln Ser Pro Ser Ser Leu Ser Ala Ser Val Gly
1               5                   10                  15

Asp Arg
```

<210> SEQ ID NO 28
<211> LENGTH: 19
<212> TYPE: PRT
<213> ORGANISM: Artificial Sequence
<220> FEATURE:
<223> OTHER INFORMATION: mAB fragment

<400> SEQUENCE: 28

```
Glu Val Gln Leu Val Glu Ser Gly Gly Gly Leu Val Gln Pro Gly Gly
1               5                   10                  15

Ser Leu Arg
```